(12) United States Patent
Xiao et al.

(10) Patent No.: US 7,556,750 B2
(45) Date of Patent: Jul. 7, 2009

US007556750B2

(54) PHOTOCHROMIC MATERIALS WITH REACTIVE SUBSTITUENTS

(75) Inventors: Wenjing Xiao, Murrysville, PA (US); Barry Van Gemert, Pitcairn, PA (US)

(73) Assignee: Transitions Optical, Inc., Pihellas Park, FL (US)

( * ) Notice: Subject to any disclaimer, the term of this patent is extended or adjusted under 35 U.S.C. 154(b) by 565 days.

(21) Appl. No.: 11/102,280

(22) Filed: Apr. 8, 2005

(65) Prior Publication Data

US 2006/0226400 A1    Oct. 12, 2006

(51) Int. Cl.
G02B 5/23 (2006.01)
G03C 1/00 (2006.01)

(52) U.S. Cl. .................. 252/586; 204/157.69; 359/4; 365/119; 430/332

(58) Field of Classification Search .................. 252/586; 359/4; 430/332; 204/157.69; 365/119
See application file for complete search history.

(56) References Cited

U.S. PATENT DOCUMENTS

| | | | |
|---|---|---|---|
| 3,933,509 A | 1/1976 | Noguchi et al. |
| 3,942,996 A | 3/1976 | Arnold et al. |
| 4,929,693 A | 5/1990 | Akashi et al. |
| 5,066,818 A | 11/1991 | Van Gemert et al. |
| 5,166,345 A | 11/1992 | Akashi et al. |
| 5,236,958 A | 8/1993 | Miyashita |
| 5,238,981 A | 8/1993 | Knowles |
| 5,252,742 A | 10/1993 | Miyashita |
| 5,274,132 A | 12/1993 | Van Gemert |
| 5,359,085 A | 10/1994 | Iwamoto et al. |
| 5,458,814 A | 10/1995 | Kumar et al. |
| 5,578,252 A | 11/1996 | Van Gemert et al. |
| 5,645,767 A | 7/1997 | Van Gemert |
| 5,645,768 A | 7/1997 | Melzig et al. |
| 5,650,098 A | 7/1997 | Kumar et al. |
| 5,651,923 A | 7/1997 | Kumar et al. |
| 5,707,557 A | 1/1998 | Melzig et al. |
| 5,723,072 A | 3/1998 | Kumar |
| 5,753,146 A | 5/1998 | Van Gemert et al. |
| 5,770,115 A | 6/1998 | Misura |
| 5,811,034 A | 9/1998 | Lin |
| 5,821,287 A | 10/1998 | Hu et al. |
| 5,952,515 A | 9/1999 | Melzig et al. |
| 5,955,520 A | 9/1999 | Heller et al. |
| 5,961,892 A | 10/1999 | Van Gemert et al. |
| 6,018,059 A | 1/2000 | Chan |
| 6,025,026 A | 2/2000 | Smith et al. |
| 6,036,890 A | 3/2000 | Melzig et al. |
| 6,068,797 A | 5/2000 | Hunt |
| 6,096,246 A | 8/2000 | Chan et al. |
| 6,113,814 A | 9/2000 | Gemert et al. |
| 6,146,554 A | 11/2000 | Melzig et al. |
| 6,150,430 A | 11/2000 | Walters et al. |
| 6,190,580 B1 | 2/2001 | Melzig et al. |
| 6,225,466 B1 | 5/2001 | Mann et al. |
| 6,296,785 B1 | 10/2001 | Nelson et al. |
| 6,340,765 B1 | 1/2002 | Momoda et al. |
| 6,392,043 B1 | 5/2002 | Bourchteine et al. |
| 6,398,987 B1 | 6/2002 | Breyne et al. |
| 6,399,791 B1 | 6/2002 | Breyne et al. |
| 6,469,076 B1 | 10/2002 | Momoda et al. |
| 6,506,322 B1 | 1/2003 | Breyne et al. |
| 6,555,028 B2 | 4/2003 | Walters et al. |
| 6,630,597 B1 | 10/2003 | Lin et al. |
| 6,683,709 B2 | 1/2004 | Mann et al. |
| 6,719,925 B1 | 4/2004 | Breyne et al. |
| 6,723,859 B2 | 4/2004 | Kawabata et al. |
| 6,747,145 B2 | 6/2004 | Zhao et al. |
| 6,846,892 B2 | 1/2005 | Kindt-Larsen et al. |
| 6,852,254 B2 | 2/2005 | Spaulding et al. |
| 6,939,007 B2 | 9/2005 | Zhao et al. |
| 6,963,003 B2 | 11/2005 | Qin |
| 7,008,568 B2 | 3/2006 | Qin |
| 7,074,943 B2 | 7/2006 | Qin |
| 7,166,357 B2 | 1/2007 | Kumar et al. |
| 7,247,262 B2 | 7/2007 | Evans et al. |
| 7,256,246 B2 | 8/2007 | Kindt-Larsen et al. |
| 7,262,295 B2 | 8/2007 | Walters et al. |
| 7,320,826 B2 | 1/2008 | Kumar et al. |
| 7,368,072 B2 | 5/2008 | Gemert et al. |

(Continued)

FOREIGN PATENT DOCUMENTS

DE    22 62 894 A    6/1974

(Continued)

OTHER PUBLICATIONS

U.S. Appl. No. 10/393,179, entitled "Photochromic Articles That Activate Behind Ultraviolet Radiation-Blocking Transparencies And Methods For Preparation," filed Mar. 20, 2003.

(Continued)

Primary Examiner—Timothy J Kugel
(74) Attorney, Agent, or Firm—Linda Pingitore; Frank P. Mallak; Deborah M. Altman

(57) ABSTRACT

Various non-limiting embodiments of the present disclosure relate to photochromic materials comprising a reactive substituent. For example, the present disclosure contemplates photochromic materials, such as photochromic naphthopyrans and indeno-fused naphthopyrans having a reactive substituent comprising a reactive moiety linked to the photochromic naphthopyran by one or more linking groups. In certain non-limiting embodiments, the reactive moiety comprises a polymerizable moiety. In other non-limiting embodiments, the reactive moiety comprises a nucleophilic moiety or an electrophilic moiety. Other non-limiting embodiments of the present disclosure relate to photochromic articles, compositions, and methods of making the photochromic articles, wherein the photochromic articles and compositions comprise the photochromic naphthopyrans described herein.

30 Claims, 2 Drawing Sheets

U.S. PATENT DOCUMENTS

| | | |
|---|---|---|
| 2001/0025948 A1 | 10/2001 | Walters et al. |
| 2001/0039356 A1 | 11/2001 | Chan et al. |
| 2003/0000028 A1 | 1/2003 | Molock et al. |
| 2003/0071247 A1 | 4/2003 | Petrovskaia et al. |
| 2003/0141490 A1 | 7/2003 | Walters et al. |
| 2003/0165686 A1 | 9/2003 | Blackburn et al. |
| 2003/0180444 A1 | 9/2003 | Takekuma et al. |
| 2003/0236376 A1 | 12/2003 | Kindt-Larsen et al. |
| 2004/0131872 A1 | 7/2004 | Fan et al. |
| 2004/0185255 A1 | 9/2004 | Walters |
| 2004/0185268 A1 | 9/2004 | Kumar et al. |
| 2004/0186241 A1 | 9/2004 | Van Gemert |
| 2004/0191520 A1 | 9/2004 | Kumar et al. |
| 2004/0197562 A1 | 10/2004 | Soane et al. |
| 2005/0012998 A1 | 1/2005 | Kumar et al. |
| 2005/0037272 A1 | 2/2005 | Tanaka |
| 2005/0175306 A1 | 8/2005 | Chong et al. |
| 2005/0258408 A1 | 11/2005 | Molock et al. |
| 2006/0022176 A1 | 2/2006 | Wang et al. |
| 2006/0090848 A1 | 5/2006 | Koga et al. |
| 2006/0100408 A1 | 5/2006 | Powell et al. |
| 2006/0110520 A1 | 5/2006 | Midorikawa et al. |
| 2006/0226400 A1 | 10/2006 | Xiao et al. |
| 2006/0226401 A1 | 10/2006 | Xiao et al. |
| 2006/0226402 A1 | 10/2006 | Kim et al. |
| 2006/0227287 A1 | 10/2006 | Molock et al. |
| 2006/0228557 A1 | 10/2006 | Kim et al. |
| 2007/0001155 A1 | 1/2007 | Walters et al. |

FOREIGN PATENT DOCUMENTS

| | | |
|---|---|---|
| DE | 196 51 286 A | 6/1997 |
| EP | 0 446 717 A2 | 9/1991 |
| EP | 1 038 870 A1 | 3/2000 |
| EP | 1 054 010 A1 | 5/2000 |
| EP | 1 184 379 A1 | 12/2000 |
| EP | 1 235 096 B1 | 8/2002 |
| FR | 2 751 648 A | 1/1998 |
| FR | 2 761 063 A | 9/1998 |
| FR | 2 800 738 A | 5/2001 |
| JP | 2000-327676 | 11/2000 |
| JP | 2004 131593 (A) | 4/2004 |
| WO | WO 97/05213 | 2/1997 |
| WO | WO 97/48993 | 12/1997 |
| WO | WO 98/28289 | 12/1997 |
| WO | WO 98/42663 A1 | 10/1998 |
| WO | WO 99/23071 | 10/1998 |
| WO | WO 00/15629 A1 | 3/2000 |
| WO | WO 00/15630 | 3/2000 |
| WO | WO 00/34805 | 6/2000 |
| WO | WO 01/60811 A1 | 12/2000 |
| WO | WO 01/19812 A1 | 3/2001 |
| WO | WO 01/32661 A1 | 5/2001 |
| WO | WO 01/36406 A1 | 5/2001 |
| WO | WO 01/94336 A1 | 12/2001 |
| WO | WO 02/057070 A2 | 7/2002 |
| WO | WO 03/020718 A1 | 3/2003 |
| WO | WO 03/044022 A2 | 5/2003 |
| WO | WO 03/077792 A2 | 9/2003 |
| WO | WO 2004/002723 A1 | 1/2004 |
| WO | WO 2004/041961 | 5/2004 |
| WO | WO 2004/047674 A2 | 6/2004 |
| WO | WO 2004/052631 A2 | 6/2004 |

OTHER PUBLICATIONS

U.S. Appl. No. 11/102,279, entitled "Photochromic Materials Having Extended Pi-Conjugated Systems and Compositions and Articles Including the Same," filed Apr. 8, 20005.

U.S. Appl. No. 11/101,979, entitled "Ophthalmic Devices Comprising Photochromic Materials With Reactive Substituents," filed Apr. 8, 2005.

U.S. Appl. No. 11/102.047, entitled "Ophthalmic Devices Comprising Photochromic Materials Having Extended Pi-Conjugated Systems," filed Apr. 8, 2005.

U.S. Appl. No. 11/102,320, entitled "Photochromic Contact Lenses And Methods For Their Production," filed Apr. 8, 2005.

U.S. Appl. No. 11/102,319, entitled "Photochromic Ophthalmic Devices Made With Dual Initiator System", filed Apr. 8, 2005.

PHOTOCHROMIC MATERIALS WITH REACTIVE SUBSTITUENTS

CROSS REFERENCE TO RELATED APPLICATIONS

Joint Research Agreement: On 1 Apr. 2003, Transitions Optical, Inc. and Johnson & Johnson Vision Care, Inc. signed an agreement for joint research and development in the field of photochromic contact lens product(s).

BACKGROUND

Various non-limiting embodiments of the present disclosure relate to photochromic materials comprising a reactive substituent. Other non-limiting embodiments of the present disclosure relate to photochromic articles, compositions, and methods of making the photochromic articles, wherein the photochromic articles and compositions comprise the photochromic materials described herein.

Many conventional photochromic materials, such as, for example, photochromic naphthopyrans, can undergo a transformation from one state to another in response to the absorption of electromagnetic radiation. For example, many conventional photochromic materials are capable of transforming between a first "clear" or "bleached" ground state and a second "colored" activated state in response to the absorption of certain wavelengths of electromagnetic radiation (or "actinic radiation"). As used herein the term "actinic radiation" refers to electromagnetic radiation that is capable of causing a photochromic material to transform from one form or state to another. The photochromic material may then revert back to the clear ground state in response to thermal energy in the absence of actinic radiation. Photochromic articles and compositions that contain one or more photochromic materials, for example photochromic lenses for eyewear applications, generally display clear and colored states that correspond to the photochromic material(s) that they contain. Thus, for example, eyewear lenses that contain photochromic materials can transform from a clear state to a colored state upon exposure to actinic radiation, such as certain wavelengths found in sunlight, and can revert back to the clear state in the absence of such radiation.

When utilized in photochromic articles and compositions, conventional photochromic materials are typically incorporated into a host polymer matrix by one of imbibing, blending and/or bonding. For example, one or more photochromic materials may be intermixed with a polymeric material or precursor thereof, and thereafter the photochromic composition may be formed into the photochromic article or, alternatively, the photochromic composition may be coated on a surface of an optical element as a thin film or layer. As used herein, the term "photochromic composition" refers to a photochromic material in combination with one or more other material, which may or may not be a photochromic material. Alternatively, the photochromic material may be imbibed into a pre-formed article or coating.

In certain circumstances it may be desirable to modify the compatibility of the photochromic material with the host polymer into which it is incorporated. For example, by making the photochromic material more compatible with the host polymer, it is less likely that the combination will demonstrate cloudiness or haze due to phase separation or migration of the photochromic material in the host polymer. In addition, compatibilized photochromic materials may be more soluble in the host polymer and/or more uniformly distributed throughout the polymer matrix. Further, by modifying the compatibility of a photochromic material with a host polymer, other properties of the photochromic composition, such as, but not limited to, fade and/or activation rate, saturated optical density, molar absorptivity or molar extinction coefficient, and activated color, may also be effected. Modifications to such properties may be done, for example, to match the same properties of complementary photochromic materials or to enable the use of such compounds in hydrophilic or hydrophobic coating compositions, thin films or in rigid to flexible plastic matrices.

One approach to modifying the compatibility of a photochromic material with a host polymer is to attach a polymerizable to the photochromic material via a polyalkoxylated linking group, for example, a polyethylene glycol, a polypropylene glycol, and/or a polybutylene glycol linking group. One potential limitation of utilizing polyalkoxylated linking groups is the degree of purity of the resultant photochromic material that can be readily achieved. For example, commercially available polyglycols that may be incorporated into the linking groups of these photochromic materials may comprise mixtures of glycol chains possessing differing numbers of glycol units within each chain. Incorporation of these commercially available polyglycols into the photochromic material may lead to mixtures of compounds differing in chain lengths and molecular weights. This may lead to difficulty in purification, since one cannot readily separate out the desired photochromic materials in these mixtures.

Further, polyalkoxylated linking groups may comprise long chains containing multiple ether oxygen functionalities, which are inherently hydrophilic. While this may present certain desirable traits with regard to compatibility with the host polymer, linking groups with differing hydrophilicities, including linking groups that may be hydrophobic or, alternatively, linking groups of shorter length, may provide for different interactions with the host polymer and the resultant photochromic article.

Accordingly, for some applications it may be desirable to develop photochromic materials that may be incorporated into a variety of host polymers and which may comprise one or more reactive substituents having polarities (i.e. hydrophilicities or lipophilicities) that may more closely match the polarities of the host polymer. In other applications, it may be desirable to develop photochromic materials comprising one or more reactive substituent having polarities that do not match the polarities of the host polymers. In addition, it may be advantageous to develop photochromic materials comprising reactive substituents of uniform composition/molecular weight that can be readily purified, such as, by crystallization, chromatography, or other methods of purification known to one skilled in the art.

BRIEF SUMMARY

Various non-limiting embodiments disclosed herein relate to photochromic materials. In one non-limiting embodiment the photochromic material comprises a photochromic naphthopyran and at least one reactive substituent bonded to the photochromic naphthopyran, wherein each reactive substituent is independently represented by one of:

-A-D-E-G-J;

-G-E-G-J;

-D-E-G-J;

-A-D-J;

-D-G-J; and

-D-J;

wherein: (i) each -A- is independently —C(=O)—, —OC(=O)—, —NHC(=O)—, or —CH$_2$—; (ii) each -D- is independently: (a) a diamine residue or a derivative thereof, said diamine residue being an aliphatic diamine residue, a cyclo aliphatic diamine residue, a diazacycloalkane residue, an azacyclo aliphatic amine residue, a diazacrown ether residue, or an aromatic diamine residue, wherein a first amine nitrogen of said diamine residue forms a bond with -A- or the photochromic naphthopyran, and a second amine nitrogen of said diamine residue forms a bond with -E-, -G-, or -J; or (b) an amino alcohol residue or a derivative thereof, said amino alcohol residue being an aliphatic amino alcohol residue, a cyclo aliphatic amino alcohol residue, an azacyclo aliphatic alcohol residue, a diazacyclo aliphatic alcohol residue, or an aromatic amino alcohol residue, wherein an amine nitrogen of said amino alcohol residue forms a bond with -A- or the photochromic naphthopyran, and an alcohol oxygen of said amino alcohol residue forms a bond with -E-, -G-, or -J; or, alternatively, the amine nitrogen of said amino alcohol residue forms a bond with -E-, -G-, or -J, and the alcohol oxygen of said amino alcohol residue forms a bond with -A- or the photochromic naphthopyran; (iii) each -E- is independently a dicarboxylic acid residue or a derivative thereof, said dicarboxylic acid residue being an aliphatic dicarboxylic acid residue, a cycloaliphatic dicarboxylic acid residue, or an aromatic dicarboxylic acid residue, wherein a first carbonyl group of said dicarboxylic acid residue forms a bond with -G- or -D-, and a second carbonyl group of said dicarboxylic acid residue forms a bond with -G-; (iv) each -G- is independently: (a) —[(OC$_2$H$_4$)$_x$(OC$_3$H$_6$)$_y$(OC$_4$H$_8$)$_z$]—O—, wherein x, y, and z, are each independently a number between 0 and 50, and the sum of x, y, and z ranges from 1 to 50; or (b) a polyol residue or a derivative thereof, said polyol residue being an aliphatic polyol residue, a cyclo aliphatic polyol residue, or an aromatic polyol residue, wherein a first polyol oxygen of said polyol residue forms a bond with -E-, -D-, or the photochromic naphthopyran, and a second polyol oxygen of said polyol residue forms a bond with -E- or -J; and (v) each -J is independently a group comprising a reactive moiety or residue thereof; or -J is hydrogen, provided that if -J is hydrogen, -J is bonded to an oxygen of group -D- or -G-, forming a reactive moiety.

Another non-limiting embodiment comprises a photochromic material represented by the formula PC—[R]$_r$, wherein (a) PC comprises a photochromic naphthopyran, wherein said photochromic naphthopyran is a 2H-naphtho[1,2-b]pyran, a 3H-naphtho[2,1-b]pyran, an indeno[2',3':3,4]naphtho[1,2-b]pyran, an indeno[1',2':4,3]naphtho[2,1-b]pyran, or a mixture thereof; (b) r is an integer ranging from 1 to 4; and (c) each R is a reactive substituent independently represented by one of:

-A-D-E-G-J;

-G-E-G-J;

-D-E-G-J;

-A-D-J;

-D-G-J; and

-D-J;

wherein: (i) each -A- is independently —C(=O)—, —OC(=O)—, —NHC(=O)—, or —CH$_2$—; (ii) each -D- is independently: (a) a diamine residue or a derivative thereof, said diamine residue being an aliphatic diamine residue, a cyclo aliphatic diamine residue, a diazacycloalkane residue, an azacyclo aliphatic amine residue, a diazacrown ether residue, or an aromatic diamine residue, wherein a first amine nitrogen of said diamine residue forms a bond with -A- or PC, and a second amine nitrogen of said diamine residue forms a bond with -E-, -G-, or -J; or (b) an amino alcohol residue or a derivative thereof, said amino alcohol residue being an aliphatic amino alcohol residue, a cyclo aliphatic amino alcohol residue, an azacyclo aliphatic alcohol residue, a diazacyclo aliphatic alcohol residue, or an aromatic amino alcohol residue, wherein an amine nitrogen of said amino alcohol residue forms a bond with -A- or PC, and an alcohol oxygen of said amino alcohol residue forms a bond with -E-, -G-, or -J; or said amine nitrogen of said amino alcohol residue forms a bond with -E-, -G-, or -J, and said alcohol oxygen of said amino alcohol residue forms a bond with -A- or PC; (iii) each -E- is independently a dicarboxylic acid residue or a derivative thereof, said dicarboxylic acid residue being an aliphatic dicarboxylic acid residue, a cycloaliphatic dicarboxylic acid residue, or an aromatic dicarboxylic acid residue, wherein a first carbonyl group of said dicarboxylic acid residue forms a bond with -G- or -D-, and a second carbonyl group of said dicarboxylic acid residue forms a bond with -G-; (iv) each -G- is independently: (a) —[(OC$_2$H$_4$)$_x$(OC$_3$H$_6$)$_y$(OC$_4$H$_8$)$_z$]—O—, wherein x, y, and z, are each independently a number between 0 and 50, and the sum of x, y, and z ranges from 1 to 50; or (b) a polyol residue or a derivative thereof, said polyol residue being an aliphatic polyol residue, a cyclo aliphatic polyol residue, or an aromatic polyol residue, wherein a first polyol oxygen of said polyol residue forms a bond with -E-, -D-, or PC, and a second polyol oxygen of said polyol residue forms a bond with -E- or -J; and (v) each -J is independently a group comprising acryl, crotyl, methacryl, 2-(methacryloxy)ethylcarbamyl, 2-(methacryloxy)ethoxycarbonyl, 4-vinylphenyl, vinyl, 1-chlorovinyl, or epoxy; or -J is hydrogen, provided that if -J is hydrogen, -J is bonded to an oxygen of group -D- or -G-.

A further non-limiting embodiment comprises a photochromic material represented by one of structures I through IV, below, or mixtures thereof.

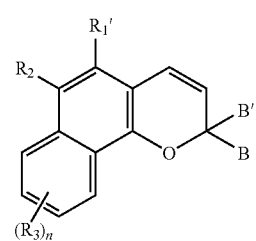

I

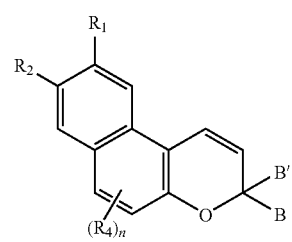

II

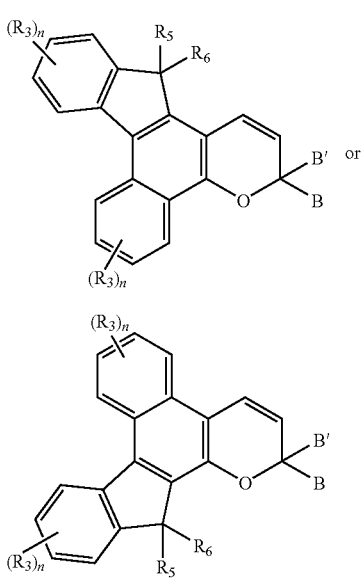

wherein, (a) $R_1$ is: a reactive substituent R, wherein said reactive substituent R is represented by one of:

-A-D-E-G-J;

-G-E-G-J;

-D-E-G-J;

-A-D-J;

-D-G-J; and

-D-J;

wherein

-A- is —C(=O)—, —OC(=O)—, —NHC(=O)—, or —CH$_2$—;

-D- is: a diamine residue or a derivative thereof, said diamine residue being an aliphatic diamine residue, a cyclo aliphatic diamine residue, a diazacycloalkane residue, an azacyclo aliphatic amine residue, a diazacrown ether residue, or an aromatic diamine residue, wherein a first amine nitrogen of said diamine residue forms a bond with -A-, structure I, structure II, structure III, or structure IV, and a second amine nitrogen of said diamine residue forms a bond with -E-, -G-, or -J; or an amino alcohol residue or a derivative thereof, said amino alcohol residue being an aliphatic amino alcohol residue, a cyclo aliphatic amino alcohol residue, an azacyclo aliphatic alcohol residue, a diazacyclo aliphatic amino alcohol residue, or an aromatic amino alcohol residue, wherein an amine nitrogen of said amino alcohol residue forms a bond with -A-, structure I, structure II, structure III, or structure IV, and an alcohol oxygen of said amino alcohol residue forms a bond with -E-, -G-, or -J; or said amine nitrogen of said amino alcohol residue forms a bond with -E-, -G-, or -J, and said alcohol oxygen of said amino alcohol residue forms a bond with -A-, structure I, structure II, structure III, or structure IV;

-E- is a dicarboxylic acid residue or a derivative thereof, said dicarboxylic acid residue being an aliphatic dicarboxylic acid residue, a cycloaliphatic dicarboxylic acid residue, or an aromatic dicarboxylic acid residue, wherein a first carbonyl group of said dicarboxylic acid residue forms a bond with -G- or -D-, and a second carbonyl group of said dicarboxylic acid residue forms a bond with -G-;

each -G- is independently: —[(OC$_2$H$_4$)$_x$(OC$_3$H$_6$)$_y$(OC$_4$H$_8$)$_z$]—O—, wherein x, y, and z, are each independently a number between 0 and 50, and the sum of x, y, and z ranges from 1 to 50; or a polyol residue or a derivative thereof, said polyol residue being an aliphatic polyol residue, a cyclo aliphatic polyol residue, or an aromatic polyol residue, wherein a first polyol oxygen of said polyol residue forms a bond with -E-, -D-, structure I, structure II, structure III, or structure IV, and a second polyol oxygen of said polyol residue forms a bond with -E- or -J; and -J is a group comprising acryl, methacryl, crotyl, 2-(methacryloxy)ethylcarbamyl, 2-(methacryloxy)ethoxycarbonyl, 4-vinylphenyl, vinyl, 1-chlorovinyl, or epoxy, or -J is hydrogen, provided that if -J is hydrogen, -J is bonded to an oxygen of group -D- or -G-;

or $R_1$ is hydrogen; hydroxy; $C_1$-$C_3$ alkyl; or the group —C(=O)W, wherein W is —OR$_7$, —N(R$_8$)R$_9$, piperidino or morpholino, wherein R$_7$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, R$_8$ and R$_9$ are each independently $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy, and said halo substituent is chloro or fluoro;

(b) $R_1'$ is: the reactive substituent R; hydrogen; hydroxy; $C_1$-$C_3$ alkyl; or the group —C(=O)W, wherein W is —OR$_7$, —N(R$_8$)R$_9$, piperidino or morpholino, wherein R$_7$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, and R$_8$ and R$_9$ are each independently $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy, and said halo substituent is chloro or fluoro;

(c) $R_2$ is the reactive substituent R; hydrogen; $C_1$-$C_6$ alkyl; $C_3$-$C_7$ cycloalkyl, substituted or unsubstituted phenyl; or —OR$_{10}$ or —OC(=O)R$_{10}$, wherein R$_{10}$ is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl ($C_1$-$C_3$)alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl, and said phenyl substituents are $C_1$-$C_6$ alkyl or $C_1$-$C_6$ alkoxy;

(d) n is an integer ranging from 0 to 4 and each $R_3$ and $R_4$ are independently for each occurrence: the reactive substituent R; hydrogen; fluoro; chloro; $C_1$-$C_6$ alkyl; $C_3$-$C_7$ cycloalkyl; substituted or unsubstituted phenyl; —OR$_{10}$ or —OC(=O)R$_{10}$, wherein R$_{10}$ is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$) alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl, and said phenyl substituents are $C_1$-$C_6$ alkyl or $C_1$-$C_6$ alkoxy; a monosubstituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —CH$_2$—, —(CH$_2$)$_t$—, or —[O—(CH$_2$)$_t$]$_k$—, wherein t is an integer 2, 3, 4, 5, or 6 and k is an integer from 1 to 50, the substituent being connected to an aryl group on another photochromic material; —N(R$_{11}$)R$_{12}$, wherein R$_{11}$ and R$_{12}$ are each independently hydrogen, C$_1$-C$_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, C$_1$-C$_8$ alkylaryl, C$_3$-C$_{20}$ cycloalkyl, C$_4$-C$_{20}$ bicycloalkyl, C$_5$-C$_{20}$ tricycloalkyl or C$_1$-C$_{20}$ alkoxyalkyl, wherein said aryl group is phenyl or naphthyl, or R$_{11}$ and R$_{12}$ come together with the nitrogen atom to form a C$_3$-C$_{20}$ hetero-bicycloalkyl ring or a C$_4$-C$_{20}$ hetero-tricycloalkyl ring; a nitrogen containing ring represented by the following graphic formula VA:

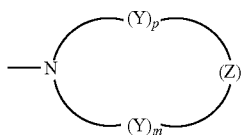

VA wherein each —Y— is independently chosen for each occurrence from —CH$_2$—, —CH(R$_{13}$)—, —C(R$_{13}$)$_2$—, —CH(aryl)-, —C(aryl)$_2$—, and —C(R$_{13}$)(aryl)-, and Z is —Y—, —O—, —S—, —S(O)—, —SO$_2$—, —NH—, —N(R$_{13}$)—, or —N(aryl)-, wherein each R$_{13}$ is independently C$_1$-C$_6$ alkyl, each aryl is independently phenyl or naphthyl, m is an integer 1, 2 or 3, and p is an integer 0, 1, 2, or 3 and when p is 0, Z is —Y—; a group represented by one of the following graphic formulae VB or VC:

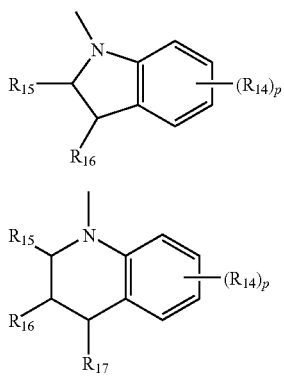

VB

VC wherein R$_{15}$, R$_{16}$, and R$_{17}$ are each independently hydrogen, C$_1$-C$_6$ alkyl, phenyl, or naphthyl, or the groups R$_{15}$ and R$_{16}$ together form a ring of 5 to 8 carbon atoms, each R$_{14}$ is independently for each occurrence from C$_1$-C$_6$ alkyl, C$_1$-C$_6$ alkoxy, fluoro, or chloro and p is an integer 0, 1, 2, or 3; and unsubstituted, mono-, or di-substituted C$_4$-C$_{18}$ spirobicyclic amine, or unsubstituted, mono- or di-substituted C$_4$-C$_{18}$ spirotricyclic amine, wherein said substituents are independently aryl, C$_1$-C$_6$ alkyl, C$_1$-C$_6$ alkoxy, or phenyl(C$_1$-C$_6$)alkyl; or an R$_3$ group in the 6-position and an R$_3$ group in the 7-position together form a group represented by one of VD and VE:

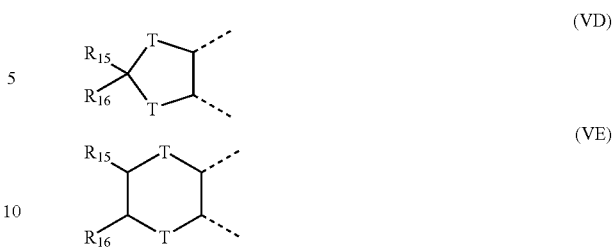

wherein T and T' are each independently oxygen or the group —NR$_{11}$—, where R$_{11}$, R$_{15}$, and R$_{16}$ are as set forth above;

(e) R$_5$ and R$_6$ are each independently: the reactive substituent R; hydrogen; hydroxy; C$_1$-C$_6$ alkyl; C$_3$-C$_7$ cycloalkyl; allyl; substituted or unsubstituted phenyl; substituted or unsubstituted benzyl; chloro; fluoro; —C(=O)W', wherein W' is hydrogen, hydroxy, C$_1$-C$_6$ alkyl, C$_1$-C$_6$ alkoxy, the unsubstituted, mono- or di-substituted aryl groups phenyl or naphthyl, phenoxy, mono- or di-(C$_1$-C$_6$)alkoxy substituted phenoxy, mono- or di-(C$_1$-C$_6$)alkoxy substituted phenoxy, amino, mono(C$_1$-C$_6$)alkylamino, di(C$_1$-C$_6$)alkylamino, phenylamino, mono- or di-(C$_1$-C$_6$)alkyl substituted phenylamino, or mono- or di-(C$_1$-C$_6$)alkoxy substituted phenylamino; —OR$_{18}$, wherein R$_{18}$ is C$_1$-C$_6$ alkyl, phenyl(C$_1$-C$_3$) alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl, C$_1$-C$_6$ alkoxy(C$_2$-C$_4$)alkyl, C$_3$-C$_7$ cycloalkyl, mono(C$_1$-C$_4$)alkyl substituted C$_3$-C$_7$ cycloalkyl, C$_1$-C$_6$ chloroalkyl, C$_1$-C$_6$ fluoroalkyl, allyl, or the group —CH(R$_{19}$)Y', wherein R$_{19}$ is hydrogen or C$_1$-C$_3$ alkyl and Y' is CN, CF$_3$, or COOR$_{20}$; wherein R$_{20}$ is hydrogen or C$_1$-C$_3$ alkyl, or R$_{18}$ is the group —C(=O)W", wherein W" is hydrogen, C$_1$-C$_6$ alkyl, C$_1$-C$_6$ alkoxy, the unsubstituted, mono- or di-substituted aryl groups phenyl or naphthyl, phenoxy, mono- or di-(C$_1$-C$_6$)alkyl substituted phenoxy, mono- or di-(C$_1$-C$_6$)alkoxy substituted phenoxy, amino, mono(C$_1$-C$_6$)alkylamino, di(C$_1$-C$_6$)alkylamino, phenylamino, mono- or di-(C$_1$-C$_6$)alkyl substituted phenylamino, or mono- or di-(C$_1$-C$_6$)alkoxy substituted phenylamino, wherein each of said phenyl, benzyl, or aryl group substituents are independently C$_1$-C$_6$ alkyl or C$_1$-C$_6$ alkoxy; or a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —CH$_2$—, —(CH$_2$)$_t$—, or —[O—(CH$_2$)$_t$]$_k$—, wherein t is an integer 2, 3, 4, 5, or 6 and k is an integer from 1 to 50, the substituent being connected to an aryl group on another photochromic material; or R$_5$ and R$_6$ together form an oxo group, a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings; and (f) B and B' are each independently: a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is the reactive substituent R; an unsubstituted, mono-, di-, or tri-substituted phenyl or aryl group; 9-julolidinyl; and an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently: hydroxyl, a group —C(=O)$R_{21}$, wherein $R_{21}$ is —O$R_{22}$, —N($R_{23}$)$R_{24}$, piperidino, or morpholino, wherein $R_{22}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, $R_{23}$ and $R_{24}$ are each independently $C_1$-$C_6$ alkyl, $C_5$-$C_7$ cycloalkyl, phenyl or substituted phenyl, the phenyl substituents being $C_1$-$C_6$ alkyl or $C_1$-$C_6$ alkoxy, and said halo substituent is chloro or fluoro, aryl, mono($C_1$-$C_{12}$)alkoxyaryl, di($C_1$-$C_{12}$)alkoxyaryl, mono($C_1$-$C_{12}$)alkylaryl, di($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$)alkyl, aryloxy($C_1$-$C_{12}$)alkoxy, mono- or di($C_1$-$C_{12}$)alkylaryl($C_1$-$C_{12}$)alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)alkoxyaryl($C_1$-$C_{12}$)alkoxy, amino, mono- or di-($C_1$-$C_{12}$)alkylamino, diarylamino, piperazine, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, or halogen; an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{12}$ alkyl, $C_1$-$C_{12}$ alkoxy, phenyl, or halogen; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —$CH_2$—, —$(CH_2)_t$—, or —[O—$(CH_2)_t]_k$—, wherein t is an integer 2, 3, 4, 5 or 6 and k is an integer from 1 to 50, the substituent being connected to an aryl group on another photochromic material; a group represented by one of:

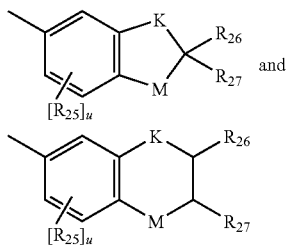

wherein K is —$CH_2$— or —O—, and M is —O— or substituted nitrogen, provided that when M is substituted nitrogen, K is —$CH_2$—, the substituted nitrogen substituents being hydrogen, $C_1$-$C_{12}$ alkyl, or $C_1$-$C_{12}$ acyl, each $R_{25}$ being independently chosen for each occurrence from $C_1$-$C_{12}$ alkyl, $C_1$-$C_{12}$ alkoxy, hydroxy, and halogen, $R_{26}$ and $R_{27}$ each being independently hydrogen or $C_1$-$C_{12}$ alkyl, and u is an integer ranging from 0 to 2; or a group represented by:

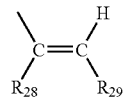

wherein $R_{28}$ is hydrogen or $C_1$-$C_{12}$ alkyl, and $R_{29}$ is an unsubstituted, mono-, or di-substituted group chosen from naphthyl, phenyl, furanyl, and thienyl, wherein the substituents are $C_1$-$C_{12}$ alkyl, $C_1$-$C_{12}$ alkoxy, or halogen; or B and B' taken together form one of a fluoren-9-ylidene, mono-, or di-substituted fluoren-9-ylidene, each of said fluoren-9-ylidene substituents being independently chosen from $C_1$-$C_{12}$ alkyl, $C_1$-$C_{12}$ alkoxy, and halogen; provided that the photochromic material comprises at least one reactive substituent R.

Still other non-limiting embodiments relate to photochromic compositions, photochromic articles, optical elements and methods of making the same, wherein the photochromic compositions, photochromic articles, and optical elements comprise a photochromic material according various non-limiting embodiments disclosed herein.

BRIEF DESCRIPTION OF THE DRAWINGS

Various non-limiting embodiments of the invention disclosed herein will be better understood when read in conjunction with the drawings, in which.

DETAILED DESCRIPTION

Figure 1:
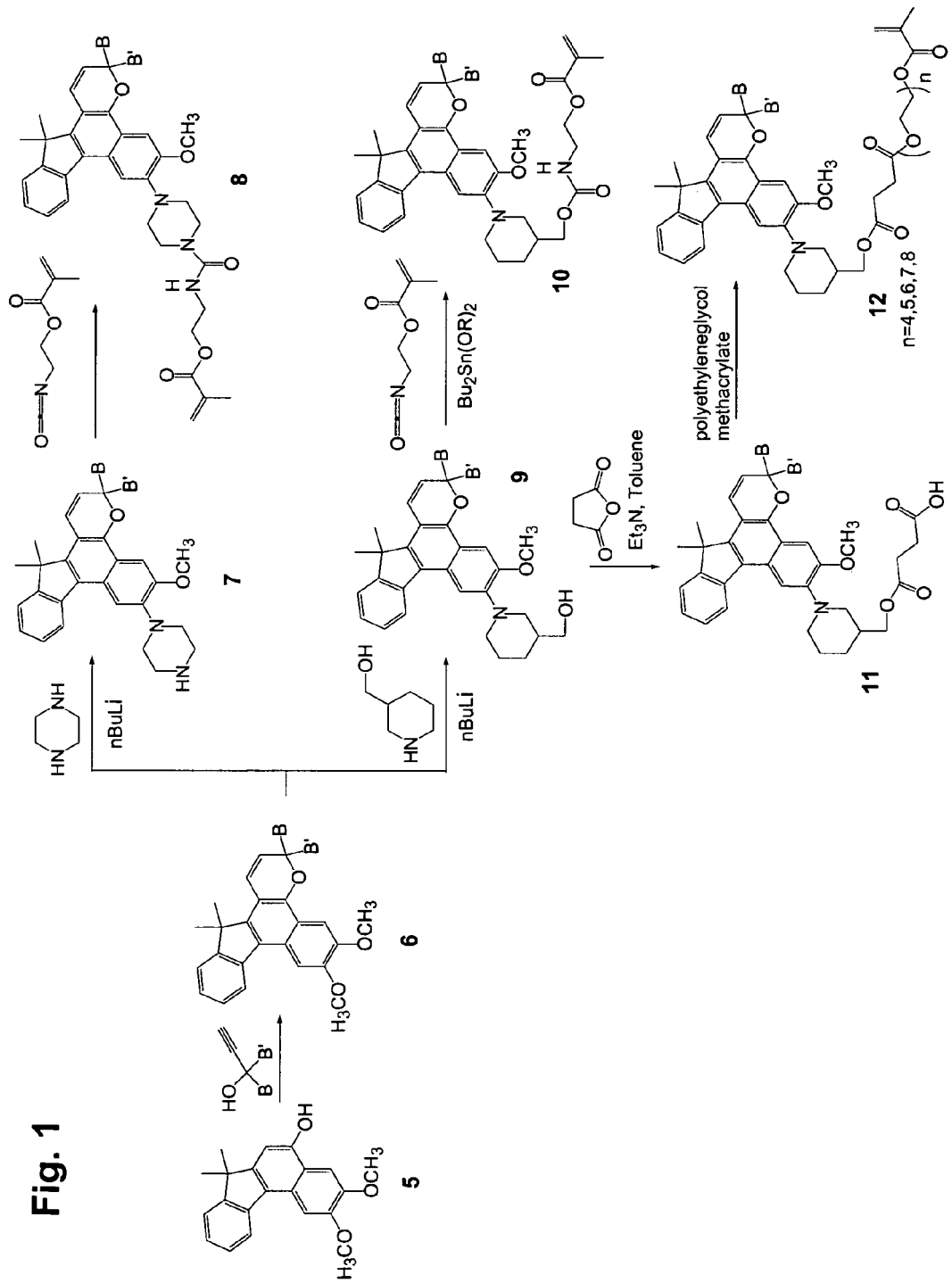
FIGS. 1 and 2 are schematic diagrams of reaction schemes for synthesizing photochromic materials according to various non-limiting embodiments disclosed herein.

As used in this specification and the appended claims, the articles "a," "an," and "the" include plural referents unless expressly and unequivocally limited to one referent.

Additionally, for the purposes of this specification, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

Photochromic materials according to various non-limiting embodiments of the invention will now be discussed. As used herein, the term "photochromic" means having an absorption spectrum for at least visible radiation that varies in response to absorption of at least actinic radiation. Further, as used herein, the term "photochromic material" means any substance that is adapted to display photochromic properties, i.e., adapted to have an absorption spectrum for at least visible radiation that varies in response to absorption of at least actinic radiation.

One non-limiting embodiment provides a photochromic material comprising a photochromic naphthopyran, and a reactive substituent bonded to the photochromic naphthopyran, wherein the reactive substituent is represented by one of:

-A-D-E-G-J;

-G-E-G-J;

-D-E-G-J;

-A-D-J;

-D-G-J; and

-D-J.

Non-limiting examples of structures for -A- according to various non-limiting embodiments of the present disclosure include —C(=O)—, —OC(=O)—, —NHC(=O)—, and —CH$_2$—.

Non-limiting examples of structures for -D- according to various non-limiting embodiments of the present disclosure include diamine residues or derivatives thereof, wherein a first amine nitrogen of said diamine residue forms a bond with -A- or the photochromic naphthopyran, and a second amine nitrogen of said diamine residue forms a bond with -E-, -G-, or -J, and amino alcohol residues or derivatives thereof, wherein an amine nitrogen of said amino alcohol residue forms a bond with -A- or the photochromic naphthopyran, and an alcohol oxygen of said amino alcohol residue forms a bond with -E-, -G-, or -J, or, alternatively, the amine nitrogen of said amino alcohol residue forms a bond with -E-, -G-, or -J, and the alcohol oxygen of said amino alcohol residue forms a bond with -A- or the photochromic naphthopyran.

In certain non-limiting embodiments where -D- is a diamine residue or a derivative thereof, non-limiting examples of said diamine residue include aliphatic diamine residues, cyclo aliphatic diamine residues, diazacycloalkane residues, azacyclo aliphatic amine residues, diazacrown ether residues, and aromatic diamine residues. Non-limiting examples of diamine residues from which -D- may be chosen include diamine residues represented by any of the following structures:

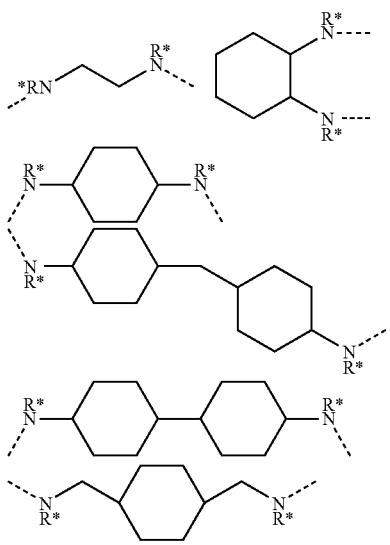

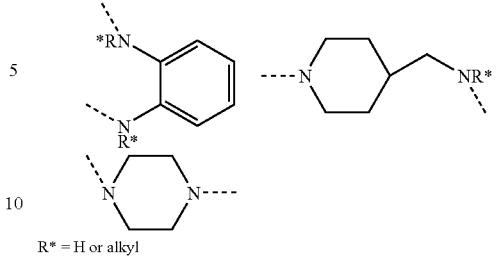

R* = H or alkyl

In other non-limiting embodiments where -D- is an amino alcohol residue or a derivative thereof, non-limiting examples of said amino alcohol residue include aliphatic amino alcohol residues, cyclo aliphatic amino alcohol residues, azacyclo aliphatic alcohol residues, diazacyclo aliphatic alcohol residues, and aromatic amino alcohol residues. Non-limiting examples of amino alcohol residues from which -D- may be chosen include amino alcohol residues represented by any of the following structures:

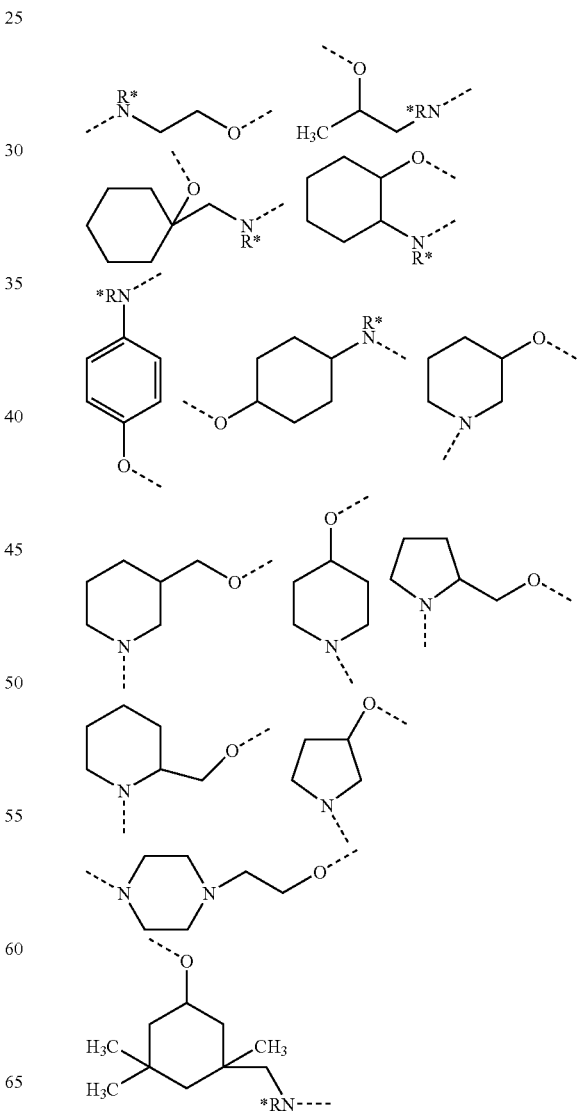

-continued

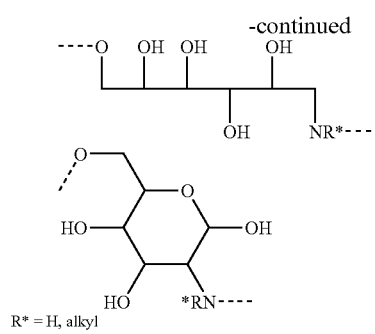

R* = H, alkyl

Non-limiting examples of structures for -E- according to various non-limiting embodiments of the present disclosure include dicarboxylic acid residues or derivatives thereof, wherein a first carbonyl group of said dicarboxylic acid residue forms a bond with -G- or -D-, and a second carbonyl group of said dicarboxylic acid residue forms a bond with -G-. Non-limiting examples of suitable dicarboxylic acid residues include aliphatic dicarboxylic acid residues, cycloaliphatic dicarboxylic acid residues, and aromatic dicarboxylic acid residues. Non-limiting examples of dicarboxylic acid residues from which -E- may be chosen include dicarboxylic residues represented by any of the following structures:

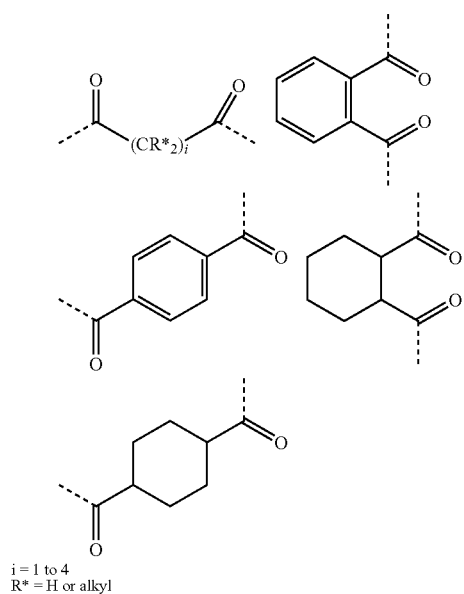

i = 1 to 4
R* = H or alkyl

Non-limiting examples of structures for -G- according to various non-limiting embodiments of the present disclosure include polyalkyleneglycol residues and polyol residues and derivatives thereof, wherein a first polyol oxygen of said polyol residue forms a bond with -E-, -D-, or the photochromic naphthopyran, and a second polyol oxygen of said polyol residue forms a bond with -E- or -J. Non-limiting examples of suitable polyalkyleneglycol residues include the structure: —[(OC$_2$H$_4$)$_x$(OC$_3$H$_6$)$_y$(OC$_4$H$_8$)]—O—, wherein x, y, and z, are each independently a number between 0 and 50, and the sum of x, y, and z ranges from 1 to 50. Non-limiting examples of suitable polyol residues include aliphatic polyol residues, cyclo aliphatic polyol residues, and aromatic polyol residues.

As discussed above, -G- can be a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue may be formed, for example and without limitation herein, by the reaction of one or more of the polyol hydroxyl groups with a precursor of -E- or -D-, such as a carboxylic acid or a methylene halide, a precursor of a polyalkoxlyated group, such as polyalkylene glycol, or a hydroxyl substituent of the indeno-fused naphthopyran. The polyol may be represented by U—(OH)$_a$ and the residue of the polyol may be represented by the formula —O—U—(OH)$_{a-1}$, wherein U is the backbone or main chain of the polyhydroxy compound and "a" is at least 2.

Examples of polyols from which -G- may be formed include polyols having at least 2 hydroxy groups such as (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

In the various non-limiting embodiments of the present disclosure, -J is a group comprising a reactive moiety or residue thereof; or -J is hydrogen, provided that if -J is hydrogen, -J is bonded to an oxygen of group -D- or -G-, forming a reactive moiety.

As used herein, the term "photochromic naphthopyran" is defined as a photochromic compound having a core naphthopyran substructure that displays photochromic properties. For example, according to various non-limiting embodiments, the photochromic naphthopyran is capable of transforming between a first "closed" form and a second "open" form in response to the absorption of actinic radiation. Examples of core naphthopyran substructures are presented below:

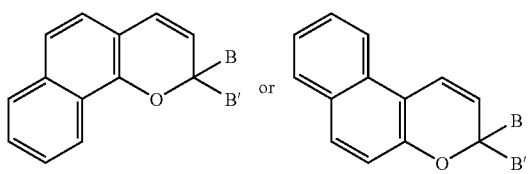

According to various non-limiting embodiments disclosed herein, the groups B and B' (shown above) are part of the photochromic naphthopyran core substructure. Without intending to be limited by any particular theory, it is believed that the B and B' groups may help stabilize the open form of the core naphthopyran substructure by being in conjugation with the pi-system of the open form of the core naphthopyran substructure. Suitable structures for B and/or B' are any structures that have at least one pi-bond that is in conjugation with the pi-system of the open form of the core naphthopyran substructure, for example, but not limited to, a substituted or unsubstituted aryl ring (e.g., a substituted or unsubstituted phenyl ring or naphthyl ring), and substituted or unsubstituted heteroaromatic ring structures. Various non-limiting examples for structure B and/or B' are discussed in detail hereinbelow.

Photochromic naphthopyrans that are suitable for use in conjunction with various non-limiting embodiments disclosed herein, include, but are not limited to, substituted 2H-naphtho[1,2-b]pyrans, substituted 3H-naphtho[2,1-b]pyrans, substituted indeno[2',3':3,4]naphtho[1,2-b]pyrans, substituted indeno[1',2':4,3]naphtho[2,1-b]pyrans, and mixtures thereof. Photochromic naphthopyrans having these structures are shown below in structures 1 through 4, respectively.

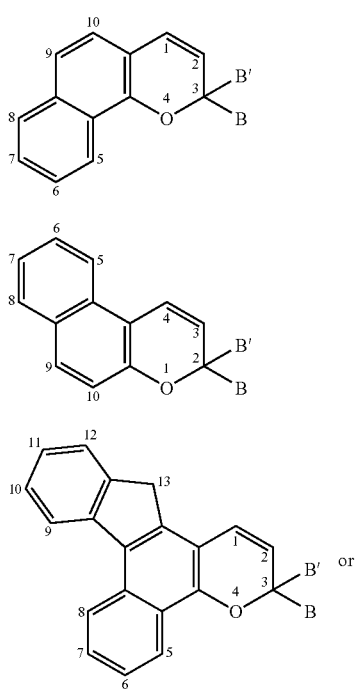

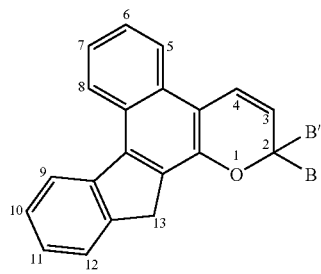

As discussed above, the photochromic materials according to various non-limiting embodiments disclosed herein, such as photochromic naphthopyrans, comprise a reactive substituent. As used herein, the term "reactive substituent" means an arrangement of atoms, wherein a portion of the arrangement comprises a reactive moiety or residue thereof. According to various non-limiting embodiments disclosed herein, the reactive substituent further comprises a linking group connecting the reactive moiety to the photochromic naphthopyran. As used herein, the term "moiety" means a part or portion of an organic molecule that has a characteristic chemical property. As used herein, the term "reactive moiety" means a part or portion of an organic molecule that may react to form one or more bonds with an intermediate in a polymerization reaction, or with a polymer into which it has been incorporated. As used herein, the phrase "intermediate in the polymerization reaction" means any combination of two or more host monomer units that are capable of reacting to form one or more bonds to additional host monomer unit(s) to continue a polymerization reaction or, alternatively, reacting with a reactive moiety of the reactive substituent on the photochromic material. For example, in one non-limiting embodiment the reactive moiety may react as a co-monomer in the polymerization reaction. Alternatively, but not limiting herein, the reactive moiety may react with the intermediate as a nucleophile or electrophile. As used herein, the term "host monomer or oligomer" means the monomeric or oligomeric material(s) into which the photochromic materials of the present disclosure may be incorporated. As used herein, the terms "oligomer" or "oligomeric material" refer to a combination of two or more monomer units that are capable of reacting with an additional monomer unit(s). As used herein, the term "linking group" means one or more group(s) or chain(s) of atoms that connect the reactive moiety to the photochromic naphthopyran. As used herein, the term "residue of a reactive moiety" means that which remains after a reactive moiety has been reacted with either a protecting group or an intermediate in a polymerization reaction. As used herein, the term "protecting group" means a group of atoms removably bonded to the reactive moiety that prevents the reactive moiety from participating in a reaction until the group is removed.

In one non-limiting embodiment, the reactive moiety comprises a polymerizable moiety. As used herein, the term "polymerizable moiety" means a part or portion of an organic molecule that can participate as a co-monomer in a polymerization reaction of a host monomer or oligomer. In another non-limiting embodiment, the reactive moiety comprises a nucleophilic moiety that reacts to form a bond with an electrophilic moiety on either the intermediate in the polymerization reaction or the host polymer. Alternatively, in another non-limiting embodiment, the reactive moiety comprises an electrophilic moiety that reacts to form a bond with a nucleophilic moiety on either the intermediate in the polymerization reaction or the host polymer. As used herein, the term "nucleophilic moiety" means an atom or grouping of atoms that is electron rich. As used herein, the term "electrophilic moiety" means an atom or grouping of atoms that is electron poor. It is appreciated by one skilled in the art that nucleophilic moieties can react with electrophilic moieties, for example to form a covalent bond therebetween.

As discussed above, in one non-limiting embodiment, the photochromic material comprises a photochromic naphthopyran and a reactive substituent bonded to the photochromic naphthopyran. The reactive substituent may be bonded to the photochromic naphthopyran at a variety of positions on the photochromic naphthopyran. Referring to the numbering scheme associated with structures 1, 2, 3, and 4 above, according to certain non-limiting embodiments, a reactive substituent may be attached to the naphthopyran as follows. For structures 1 or 2, a reactive substituent may be bonded to the naphthopyran at any of the positions numbered 5 through 10. For structures 3 or 4, a reactive substituent may be bonded to the indeno-fused naphthopyran at any of the positions numbered 5 through 13. In addition, for structures 1, 2, 3, and 4, a reactive substituent may additionally or alternatively be bonded to group B and/or group B'.

For example, according to various non-limiting embodiments disclosed herein wherein the photochromic naphthopyran comprises a 2H-naphtho[1,2-b]pyran or a 3H-naphtho[2,1-b]pyran, structures 1 or 2 respectively, a reactive substituent may be bonded to the photochromic naphthopyran by replacing a hydrogen on the rings of the naphthoportion of the photochromic naphthopyran with a reactive substituent. Alternatively or in addition, a reactive substituent may be bonded to photochromic naphthopyran 1 or 2 by replacing a hydrogen on the B and/or B' groups of the photochromic naphthopyran with a reactive substituent. According to other non-limiting embodiments, wherein the photochromic naphthopyran comprises an indeno[2',3':3,4]naphtho[1,2-b]pyran or an indeno[1',2':4,3]naphtho[2,1-b]pyran, structures 3 or 4 respectively, a reactive substituent may be bonded to the photochromic naphthopyran by replacing a hydrogen on the rings of the indeno-fused naphtho-portion of the photochromic naphthopyran with a reactive substituent. Alternatively or in addition, a reactive substituent may be bonded to photochromic naphthopyran 3 or 4 by replacing a hydrogen on the B and/or B' groups of the photochromic naphthopyran with a reactive substituent.

As discussed above, according to various non-limiting embodiments disclosed herein, the reactive substituent may be represented by one of the following structures:

-A-D-E-G-J;

-G-E-G-J;

-D-E-G-J;

-A-D-J;

-D-G-J; and

-D-J;

wherein the groups -A-, -D-, -E-, and -G- are as set forth above, and -J is a group comprising a reactive moiety or residue of a reactive moiety; or -J is hydrogen, provided that if -J is hydrogen, -J is bonded to an oxygen of group -D- or -G-, forming a reactive moiety. The -J group may comprise any moiety capable of reacting with an intermediate in the polymerization reaction or the host monomer. For example, in one non-limiting embodiment, the -J group comprises a polymerizable moiety that can react as a co-monomer in an addition-type polymerization reaction or a condensation-type polymerization reaction of the host monomer, resulting in a co-polymer of the photochromic material and the host polymer. As used herein, the term "addition-type polymerization reaction" means a polymerization reaction in which the resultant polymer contains all of the atoms originally present in the monomer units. As used herein, the term "condensation-type polymerization reaction" means a polymerization reaction in which the resultant polymer does not contain all of the atoms originally present in the monomer units. As used herein, the term "host polymer" means the polymer that results from polymerization of the host monomer. For example, in certain non-limiting embodiments, the host polymer may include polymers that may contain a functionality that can react to form a bond with a reactive substituent on the photochromic material. In other non-limiting embodiments, the host polymer may be the polymer in which the photochromic material is incorporated within or otherwise co-polymerized with or bonded to. In another non-limiting embodiment, the -J group comprises a nucleophilic or electrophilic moiety that can react with an electrophilic or nucleophilic moiety, respectively, on an intermediate in the polymerization reaction or on the host polymer. In another non-limiting embodiment, -J comprises a hydrogen, provided that when -J is hydrogen, -J is bonded to an oxygen of group -D- or -G-, forming a reactive moiety, i.e., a hydroxyl group.

When -J is bonded to an oxygen or a nitrogen, reactive moieties suitable for use in various non-limiting embodiments of the present disclosure include, but are not limited to, acryl, methacryl, crotyl, 2-(methacryloxy)ethylcarbamyl, 2-(methacryloxy)ethoxycarbonyl, 4-vinylphenyl, vinyl, 1-chlorovinyl, and epoxy. Structures corresponding to such reactive moieties are shown below:

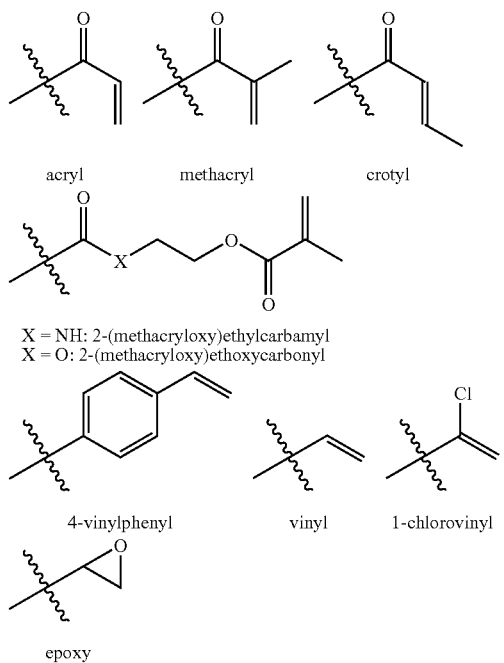

Alternatively, -J may be hydrogen, provided that if -J is hydrogen, -J is bonded to an oxygen, such that the linkage is terminated by a reactive hydroxyl group, wherein the hydroxyl group comprises the reactive moiety.

As indicated above, the reactive substituent according to various non-limiting embodiments disclosed herein may comprise one or more groups -A-, -D-, -E-, and -G- which connect the group -J to the photochromic naphthopyran. As used herein, linking groups, as defined above, may comprise one or more of the groups -A-, -D-, -E-, and -G-. That is, various combinations of groups -A-, -D-, -E-, and -G- can form the linking group portion of the reactive substituent. As defined herein, the term "group" or "groups" means an arrangement of one or more atoms.

The structure of the linking groups of the various non-limiting embodiments will now be discussed in detail. As discussed above, the linking group portion of the reactive substituent comprises various combinations of the groups -A-, -D-, -E-, and -G-. For example, in certain non-limiting embodiments, the linking group portion of the reactive substituent comprises: -A-D-E-G-, -G-E-G-, -D-E-G-, -A-D-, -D-G-, or -D-, wherein a first group of the linking group is bonded to the photochromic naphthopyran at a position as set forth above and a second group of the linking group is bonded to the -J group as discussed in detail below. It will be understood by one having skill in the art that linking groups comprising various combinations of the groups -A-, -D-, -E-, and -G- can be synthesized by a variety of methods and the bond connections discussed below are for illustration purposes only and are in no way intended to imply a particular required or preferred synthetic approach to making the reactive substituent.

The connections between the various groups, i.e., -A-, -D-, -E-, and -G-, according to various non-limiting embodiments will now be discussed. In one non-limiting embodiment, the -A- group forms a bond with the photochromic naphthopyran and a bond with the -D- group. According to this non-limiting embodiment, the A-D bond may be a covalent bond between the carbonyl or methylene carbon of the -A- group and a nitrogen or oxygen of the diamine residue or amino alcohol residue of the -D- group. For example, according to various non-limiting embodiments, when -A- comprises a carbonyl carbon, the A-D bond may be an amide or an ester bond. In another non-limiting embodiment, when -A- comprises a methylene carbon, the A-D bond may be an amine or ether bond. As used herein, the term "methylene" means an organic group having the structure —$CH_2$—.

In other non-limiting embodiments, the -D- group forms a bond with an -A- group (as described above) or the photochromic naphthopyran and a bond with an -E- or -G- group. According to one non-limiting embodiment, the D-E bond may be a covalent bond between a nitrogen or oxygen of the diamine residue or amino alcohol residue of the -D- group and the carbonyl carbon of one of the carboxylic acid residues of the -E- group, forming an amide or ester bond therebetween. According to another non-limiting embodiment, the D-G bond may be a covalent bond wherein the nitrogen or oxygen of the diamine residue or amino alcohol residue of the -D- group replaces a terminal oxygen residue on the polyol residue or polyalkyleneglycol residue of the -G- group, thereby forming an amine or ether bond.

In other non-limiting embodiments, the -E- group forms a bond with a -D- group (as described above) or a first -G- group and a bond with a second -G- group. According to these non-limiting embodiments, the E-G bond may be a covalent bond between a terminal oxygen residue on the polyol residue or polyalkyleneglycol residue of the -G- group and the carbonyl carbon of one of the carboxylic acid residues of the -E- group, forming an ester bond therebetween.

As previously discussed, the physical and chemical nature of linking groups may have an effect on the overall properties of the photochromic material. For example, in one non-limiting embodiment, the linking groups of the reactive substituent may have a hydrophilic nature such that the photochromic material may be more readily soluble in hydrophilic or polar host monomers. In another non-limiting embodiment, the linking groups of the reactive substituent may have a lipophilic nature such that the photochromic material may be more readily soluble in lipophilic or nonpolar host monomers.

The linking groups according to certain non-limiting embodiments of the present disclosure may also be of a uniform length and/or composition such that the resultant photochromic material may be more readily purified, when compared to a photochromic material having linking groups of non-uniform length. For example, in certain non-limiting embodiments where the linking group is of a uniform length and/or composition, the resultant photochromic material may be crystalline and therefore may be purified by recrystallization. In other non-limiting embodiments, where the linking group is of a uniform length and/or composition, the resultant photochromic material may be readily purified by chromatographic methods or other methods of purification known to one skilled in the art. For example, in one non-limiting embodiment set forth in Example 3, the photochromic material (i.e., 3-phenyl-3-(4-morpholinophenyl)-6-methoxy-7-(4-(2-methacryloxyethyl)carbamylpiperizin-1-yl)-13,13-dimethyl-3H,13H-indeno[2',3':3,4]naphtho[1,2-b]pyran) comprises a photochromic naphthopyran with a reactive substituent corresponding to -D-J. According to this non-limiting embodiment, the photochromic material may be purified by crystallization with an ethyl acetate/hexanes mixture to yield purple-tinted crystals. In another non-limiting embodiment set forth in Example 5, the photochromic material (i.e., 3-phenyl-3-(4-(4-(2-methacryloxyethyl)carbamylpiperazin-1-yl)phenyl)-6,11-dimethoxy-13,13-dimethyl-3H,13H-indeno[2',3':3,4]naphtho[1,2-b]pyran) comprises a photochromic naphthopyran with a reactive substituent corresponding to -D-J. According to this non-limiting embodiment, the photochromic material may be purified by silica gel chromatography to yield a green expanded foam solid. In other non-limiting embodiments, an intermediate in the synthesis of the photochromic material may be readily purified by recrystallization methods, chromatographic methods or other methods of purification know to one skilled in the art.

Bonding between the various linking group(s) and the group -J will now be discussed. According to various non-limiting embodiments disclosed herein, the group -J may be bonded to the linking group by a G-J bond or a D-J bond. In certain non-limiting embodiments where the reactive moiety -J is bonded to the linking group by a G-J bond, the G-J bond may have many possible structures. For example, when -J is acryl, methacryl, or crotyl, the G-J bond may be an ester bond, that is, a terminal oxygen residue of the -G- group bonds with the carbonyl of the -J group. Alternatively, when -J is 2-(methacryloxy) ethylcarbamyl or 2-(methacryloxy)ethoxycarbonyl, the G-J bond may be a carbamate and carbonate bond, respectively, where a terminal oxygen residue of the -G- group bonds with the carbonyl of the ethyl carbamyl or ethoxycarbonyl portion of the -J group. Further, when -J is 4-vinylphenyl, vinyl, 1-chlorovinyl or epoxy, the G-J bond may be an ether bond between a terminal oxygen residue of the -G- group and the carbon of the -J group. In certain non-limiting embodiments, the -J group may be a hydrogen, such that the G-J bond is an oxygen-hydrogen bond resulting in a reactive moiety, i.e., a hydroxyl group, on the linking group.

In other non-limiting embodiments where the reactive moiety -J is bonded to the linking group by a D-J bond, the D-J bond may have many possible structures. For example, when -J is acryl, methacryl, or crotyl, the D-J bond may be an ester or amide bond, that is, an alcohol oxygen or an amine nitrogen on the amino alcohol residue or diamine residue of the -D- group bonds with the carbonyl of the -J group. Alternatively, when -J is 2-(methacryloxy)ethylcarbamyl or 2-(methacryloxy)ethoxycarbonyl, the D-J bond may be a urea, carbamate, or carbonate bond, where an amine nitrogen on the diamine residue or amino alcohol residue, or an alcohol oxygen on the amino alcohol residue of the -D- group bonds with the carbonyl of the ethylcarbamyl or ethoxycarbonyl portion of the -J group. Further, when -J is 4-vinylphenyl, vinyl, 1-chlorovinyl or epoxy, the D-J may be an amine or ether bond between an amine nitrogen or the alcohol oxygen, respectively, of the -D- group and the carbon of the -J group. In certain non-limiting embodiments, when -D- is an amino alcohol, the -J group may be a hydrogen bonded to the oxygen of the amino alcohol residue, such that the D-J bond is an oxygen-hydrogen bond, resulting in a reactive moiety, i.e., a hydroxyl group, on the linking group.

According to various non-limiting embodiments disclosed herein, wherein -J is acryl, methacryl, 2-(methacryloxy)ethylcarbamyl or epoxy, -J may be attached to the -D- or -G- group of the linking group by condensation of -D- or -G- with acryloyl chloride, methacryloyl chloride, 2-isocyanatoethyl methacrylate or epichlorohydrin, respectively.

Another non-limiting embodiment provides a photochromic material represented by:

PC—[R]$_r$ wherein: (a) PC comprises a photochromic naphthopyran, which may be for example, without limitation, a 2H-naphtho[1,2-b]pyran, a 3H-naphtho[2,1-b]pyran, an indeno[2',3':3,4]naphtho[1,2-b]pyran, an indeno[1',2':4,3]naphtho[2,1-b]pyran, or a mixture thereof; (b) r is an integer ranging from 1 to 4; and (c) R is a reactive substituent represented by one of:

-A-D-E-G-J;

-G-E-G-J;

-D-E-G-J;

-A-D-J;

-D-G-J; and

-D-J;

wherein the groups -A-, -D-, -E-, and -G- are as set forth above, and -J is a group comprising a reactive moiety or residue thereof; or -J is hydrogen, provided that if -J is hydrogen, -J is bonded to an oxygen of group -D- or -G-, forming a reactive moiety. Non-limiting examples of -J, according to certain non-limiting embodiments, include acryl, crotyl, methacryl, 2-(methacryloxy)ethylcarbamyl, 2-(methacryloxy)ethoxycarbonyl, 4-vinylphenyl, vinyl, 1-chlorovinyl, and epoxy.

As discussed with respect to the various non-limiting embodiments set forth above, the reactive substituent R according to this non-limiting embodiment may be bonded to the photochromic naphthopyran PC in a variety of positions. For example, when PC is a 2H-naphtho[1,2-b]pyran or a 3H-naphtho[2,1-b]pyran, a reactive substituent R may be bonded at any of the positions numbered 5 through 10 according to structures 1 or 2 above. When PC is an indeno[2',3':3,4]naphtho[1,2-b]pyran or an indeno[1',2':4,3]naphtho[2,1-b]pyran, a reactive substituent R may be bonded at any of the positions numbered 5 through 13 according to structures 3 or 4 above. In addition or alternatively, when PC is a 2H-naphtho[1,2-b]pyran, a 3H-naphtho[2,1-b]pyran naphthopyran, an indeno[2',3':3,4]naphtho[1,2-b]pyran or an indeno[1',2':4,3]naphtho[2,1-b]pyran, a reactive substituent R may be bonded to group B and/or group B'.

Further, as indicated above, the photochromic materials according to various non-limiting embodiments disclosed herein may comprises one reactive substituent R or may comprise multiple reactive substituents R, each of which may be the same or different. For example, according to one non-limiting embodiment wherein r is 2, the photochromic materials comprise two reactive substituents R, which may be the same or different, and which may be bonded to the photochromic naphthopyran PC at two of the numbered positions set forth above, at one of the numbered positions and on one of the B or B' groups, or both R substituents may be bonded to the photochromic naphthopyran PC at the B and/or B' group.

According to still other non-limiting embodiments disclosed herein, the photochromic material comprising at least one reactive substituent can be represented by the following structures I through IV, or a mixture thereof:

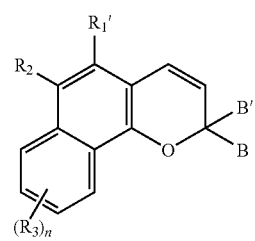

I

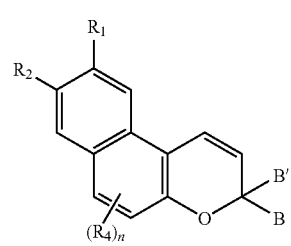

II

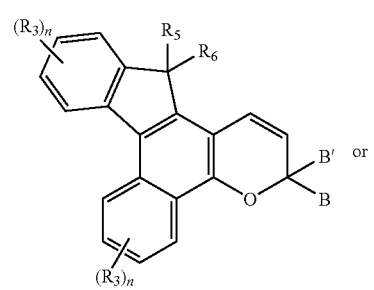

III

-continued

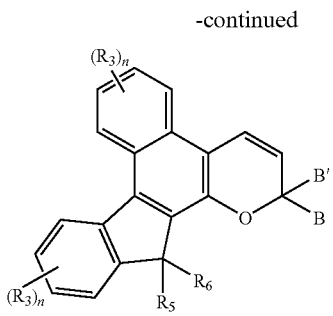

IV

Referring to structure II above, according to various non-limiting embodiments of the present disclosure, non-limiting examples for the structure of group $R_1$ include: the reactive substituent R; hydrogen; hydroxy; $C_1$-$C_3$ alkyl; and the group, —C(=O)W, wherein W is —$OR_7$, —$N(R_8)R_9$, piperidino or morpholino, wherein $R_7$ is allyl, $C_1$-$C_6$ alkyl, phenyl, mono($C_1$-$C_6$)alkyl substituted phenyl, mono($C_1$-$C_6$) alkoxy substituted phenyl, phenyl($C_1$-$C_3$)alkyl, mono($C_1$-$C_6$)alkyl substituted phenyl($C_1$-$C_3$)alkyl, mono($C_1$-$C_6$) alkoxy substituted phenyl($C_1$-$C_3$)alkyl, $C_1$-$C_6$ alkoxy($C_2$-$C_4$) alkyl or $C_1$-$C_6$ haloalkyl, $R_8$ and $R_9$ are each independently chosen from $C_1$-$C_6$ alkyl, $C_5$-$C_7$ cycloalkyl, phenyl, mono-substituted phenyl, and di-substituted phenyl, said phenyl substituents are $C_1$-$C_6$ alkyl or $C_1$-$C_6$ alkoxy, and said halo substituent are chloro or fluoro.

Referring now to structure I above, according to various non-limiting embodiments of the present disclosure, non-limiting examples for the structure of group $R_1'$ include: the reactive substituent R; hydrogen; hydroxy; $C_1$-$C_3$ alkyl; and the group —C(=O)W, wherein W is —$OR_7$, —$N(R_8)R_9$, piperidino or morpholino, wherein $R_7$ is allyl, $C_1$-$C_6$ alkyl, phenyl, mono($C_1$-$C_6$)alkyl substituted phenyl, mono($C_1$-$C_6$) alkoxy substituted phenyl, phenyl($C_1$-$C_3$)alkyl, mono($C_1$-$C_6$)alkyl substituted phenyl($C_1$-$C_3$)alkyl, mono($C_1$-$C_6$) alkoxy substituted phenyl($C_1$-$C_3$)alkyl, $C_1$-$C_6$ alkoxy($C_2$-$C_4$) alkyl or $C_1$-$C_6$ haloalkyl, and $R_8$ and $R_9$ are each independently chosen from $C_1$-$C_6$ alkyl, $C_5$-$C_7$ cycloalkyl, phenyl, mono-substituted phenyl, and di-substituted phenyl, wherein said phenyl substituents are $C_1$-$C_6$ alkyl or $C_1$-$C_6$ alkoxy, and said halo substituent are chloro or fluoro.

Referring now to structures I and II above, according to various non-limiting embodiments of the present disclosure, non-limiting examples for the structure of group $R_2$ include: the reactive substituent R; hydrogen; $C_1$-$C_6$ alkyl; $C_3$-$C_7$ cycloalkyl; substituted or unsubstituted phenyl; and —$OR_{10}$ or —OC(=O)$R_{10}$, wherein $R_{10}$ is hydrogen, $C_1$-$C_6$ alkyl, phenyl($C_1$-$C_3$)alkyl, mono($C_1$-$C_6$)alkyl substituted phenyl ($C_1$-$C_3$)alkyl, mono($C_1$-$C_6$)alkoxy substituted phenyl($C_1$-$C_3$)alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl, and said phenyl substituents are $C_1$-$C_6$ alkyl or $C_1$-$C_6$ alkoxy.

Referring now to structures I, II, III, and IV above, in various non-limiting embodiments of the present disclosure, non-limiting examples of structures for each $R_3$ and each $R_4$ independently include: the reactive substituent R; hydrogen; fluoro; chloro; $C_1$-$C_6$ alkyl; $C_3$-$C_7$ cycloalkyl; substituted or unsubstituted phenyl; —$OR_{10}$ or —OC(=O)$R_{10}$, wherein $R_{10}$ is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$) alkoxy substituted phenyl($C_1$-$C_3$)alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl, and said phenyl substituents are $C_1$-$C_6$ alkyl or $C_1$-$C_6$ alkoxy; and a mono-substituted phenyl, said phenyl having a substituent located at the para position, wherein the substituent is: a dicarboxylic acid residue or derivative thereof, a diamine residue or derivative thereof, a amino alcohol residue or derivative thereof, a polyol residue or derivative thereof, —$CH_2$—, —($CH_2$)$_t$—, or —[O—($CH_2$)$_t$]$_k$—, wherein t is an integer 2, 3, 4, 5, or 6 and k is an integer from 1 to 50, the substituent being connected to an aryl group on another photochromic material. For structures I, II, III, and IV, n is an integer from 1 to 4.

Other non-limiting examples of structures for each $R_3$ and each $R_4$ include a nitrogen containing group, wherein the nitrogen containing group may be —N($R_{11}$)$R_{12}$, wherein $R_{11}$ and $R_{12}$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}$ and $R_{12}$ come together with the nitrogen atom to form a $C_3$-$C_{20}$ hetero-bicycloalkyl ring or a $C_4$-$C_{20}$ hetero-tricycloalkyl ring; a nitrogen containing ring represented by the following graphic formula VA:

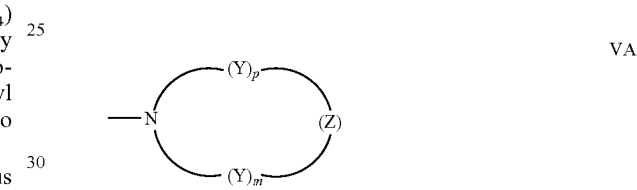

VA wherein each —Y— is independently for each occurrence —$CH_2$—, —CH($R_{13}$)—, —C($R_{13}$)$_2$—, —CH(aryl)-, —C(aryl)$_2$-, or —C($R_{13}$)(aryl)-, and Z is —Y—, —O—, —S—, —S(O)—, —$SO_2$—, —NH—, —N($R_{13}$)—, or —N(aryl)-, wherein each $R_{13}$ is independently $C_1$-$C_6$ alkyl, each aryl is independently phenyl or naphthyl, m is an integer 1, 2, or 3, and p is an integer 0, 1, 2, or 3 and when p is 0, Z is —Y—; a group represented by one of the following graphic formulae VB or VC:

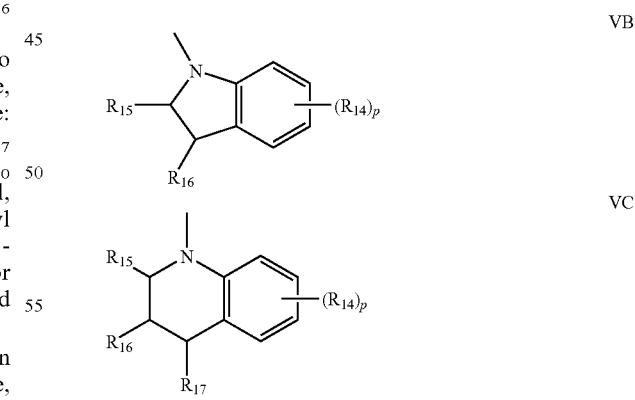

VB

VC wherein $R_{15}$, $R_{16}$, and $R_{17}$ are each independently hydrogen, $C_1$-$C_6$ alkyl, phenyl, or naphthyl, or $R_{15}$ and $R_{16}$ together may form a ring of 5 to 8 carbon atoms and each $R_{14}$ is independently for each occurrence from $C_1$-$C_6$ alkyl, $C_1$-$C_6$ alkoxy, fluoro or chloro and p is an integer 0, 1, 2, or 3; unsubstituted, mono-, or di-substituted $C_4$-$C_{18}$ spirobicyclic amine; and unsubstituted, mono-, or di-substituted $C_4$-$C_{18}$ spirotricyclic amine; wherein said spirobicyclic and spirotricyclic amine substituents are independently for each occurrence aryl, $C_1$-$C_6$ alkyl, $C_1$-$C_6$ alkoxy, or phenyl($C_1$-$C_6$)alkyl.

Alternatively, according to various non-limiting embodiments disclosed herein, an $R_3$ group in the 6-position and an $R_3$ group in the 7-position, according to the numbering set forth in structures 1, 2, 3, and 4 above, together form a group represented by graphic formulae VD or VE:

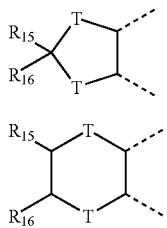

(VD)

(VE)

wherein T and T' are each independently oxygen or the group —$NR_{11}$—, where $R_{11}$, $R_{15}$, and $R_{16}$ are as set forth above.

Referring now to structures III and IV above, according to various non-limiting embodiments of the present disclosure, non-limiting examples of the structure for each of groups $R_5$ and $R_6$ may independently include: the reactive substituent R; hydrogen; hydroxy; $C_1$-$C_6$ alkyl; $C_3$-$C_7$ cycloalkyl; allyl; phenyl; mono-substituted phenyl; benzyl; mono-substituted benzyl; chloro; fluoro; the group —C(=O)W', wherein W' is hydroxy, $C_1$-$C_6$ alkyl, $C_1$-$C_6$ alkoxy, phenyl, mono-substituted phenyl, amino, mono($C_1$-$C_6$)alkylamino, or di($C_1$-$C_6$)alkylamino; —$OR_{18}$, wherein $R_{18}$ is $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, or the group, —CH($R_{19}$)Y', wherein $R_{19}$ is hydrogen or $C_1$-$C_3$ alkyl and Y' is CN, $CF_3$, or $COOR_{20}$, wherein $R_{20}$ is hydrogen or $C_1$-$C_3$ alkyl, or $R_{18}$ is the group, —C(=O)W", wherein W" is hydrogen, $C_1$-$C_6$ alkyl, $C_1$-$C_6$ alkoxy, the unsubstituted, mono-, or di-substituted aryl groups phenyl or naphthyl, phenoxy, mono- or di-($C_1$-$C_6$)alkyl substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, wherein each of said phenyl, benzyl or aryl group substituents are independently $C_1$-$C_6$ alkyl or $C_1$-$C_6$ alkoxy; and a mono-substituted phenyl, said phenyl having a substituent located at the para position, wherein the substituent is: a dicarboxylic acid residue or derivative thereof, a diamine residue or derivative thereof, a amino alcohol residue or derivative thereof, a polyol residue or derivative thereof, —$CH_2$—, —$(CH_2)_t$—, or —[O—$(CH_2)_t]_k$—, wherein t is an integer 2, 3, 4, 5, or 6 and k is an integer from 1 to 50, the substituent being connected to an aryl group on another photochromic material.

Alternatively, in certain non-limiting embodiments, $R_5$ and $R_6$ can together form an oxo group, a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1, or 2 benzene rings.

Referring again to structures I, II, III, and IV above, according to various non-limiting embodiments, non-limiting examples of the structure of the groups B and B' may each independently include: a substituted phenyl; a substituted aryl; a substituted 9-julolindinyl; a substituted heteroaromatic group, such as pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl, wherein one or more phenyl, aryl, 9-julolindinyl, or heteroaromatic substituent is the reactive substituent R; an unsubstituted, mono-, di-, or tri-substituted phenyl or aryl group; 9-julolidinyl; or an unsubstituted, mono- or di-substituted heteroaromatic group, such as pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl or fluorenyl, wherein each of the phenyl, aryl and heteroaromatic substituents are independently chosen from: hydroxyl, a group —C(=O)$R_{21}$, wherein $R_{21}$ is —$OR_{22}$, —N($R_{23}$)$R_{24}$, piperidino, or morpholino, wherein $R_{22}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, and $R_{23}$ and $R_{24}$ are each independently $C_1$-$C_6$ alkyl, $C_5$-$C_7$ cycloalkyl, phenyl or substituted phenyl, wherein the phenyl substituents are $C_1$-$C_6$ alkyl or $C_1$-$C_6$ alkoxy, and said halo substituent are chloro or fluoro, and aryl, mono($C_1$-$C_{12}$)alkoxyaryl, di($C_1$-$C_{12}$)alkoxyaryl, mono($C_1$-$C_{12}$)alkylaryl, di($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$)alkyl, aryloxy($C_1$-$C_{12}$)alkoxy, mono- or di($C_1$-$C_{12}$)alkylaryl($C_1$-$C_{12}$)alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)alkoxyaryl($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, and halogen; an unsubstituted or mono-substituted group, such as pyrazolyl, imidazolyl, pyrazolinyl, imidazolinyl, pyrrolinyl, phenothiazinyl, phenoxazinyl, phenazinyl, or acridinyl, wherein each of said substituents are independently $C_1$-$C_{12}$ alkyl, $C_1$-$C_{12}$ alkoxy, phenyl, or halogen; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —$CH_2$—, —$(CH_2)_t$—, or —[O—$(CH_2)_t]_k$—, wherein t is an integer 2, 3, 4, 5, or 6 and k is an integer from 1 to 50, the substituent being connected to an aryl group on another photochromic material; a group represented by one of:

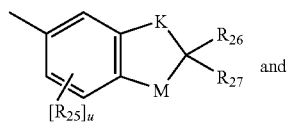 and

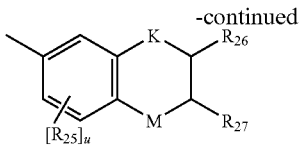

wherein K is —CH$_2$— or —O—, and M is —O— or substituted nitrogen, provided that when M is substituted nitrogen, K is —CH$_2$—, the substituted nitrogen substituents are hydrogen, C$_1$-C$_{12}$ alkyl, or C$_1$-C$_{12}$ acyl, each R$_{25}$ is independently for each occurrence C$_1$-C$_{12}$ alkyl, C$_1$-C$_{12}$ alkoxy, hydroxy, or halogen, R$_{26}$ and R$_{27}$ each are independently hydrogen or C$_1$-C$_{12}$ alkyl; and u is the integer 0, 1, or 2; or a group represented by:

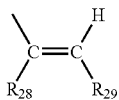

wherein R$_{28}$ is hydrogen or C$_1$-C$_{12}$ alkyl, and R$_{29}$ is an unsubstituted, mono-, or di-substituted group, such as naphthyl, phenyl, furanyl, or thienyl, wherein the substituents are independently C$_1$-C$_{12}$ alkyl, C$_1$-C$_{12}$ alkoxy, or halogen.

Alternatively according to certain non-limiting embodiments, B and B' taken together form an unsubstituted, mono-, or di-substituted fluoren-9-ylidene, each of said fluoren-9-ylidene substituents are independently C$_1$-C$_{12}$ alkyl, C$_1$-C$_{12}$ alkoxy, or halogen.

For each of the groups R$_1$, R$_1$', R$_2$, R$_3$, R$_4$, R$_5$, R$_6$, B, and B' discussed above, wherein the group comprises the reactive substituent R, each reactive substituent R can be independently chosen from and represented by one of:

-A-D-E-G-J;

-G-E-G-J;

-D-E-G-J;

-A-D-J;

-D-G-J; and

-D-J.

Non-limiting examples of structures for -A- according to various non-limiting embodiments of the present disclosure include —C(=O)—, —OC(=O)—, —NHC(=O)—, and —CH$_2$—.

Non-limiting examples of structures for -D- according to various non-limiting embodiments of the present disclosure include diamine residues or derivatives thereof, and amino alcohol residues or derivatives thereof as set forth above.

In certain non-limiting embodiments where -D- is a diamine residue or a derivative thereof, a first amine nitrogen of the diamine residue may form a bond with -A-, structure I, structure II, structure III, or structure IV, and a second amine nitrogen of the diamine residue may form a bond with -E-, -G-, or -J. In other non-limiting embodiments where -D- is a amino alcohol residue or a derivative thereof, the amine nitrogen of the amino alcohol residue may form a bond with -A-, structure I, structure II, structure III, or structure IV, and the alcohol oxygen of the amino alcohol residue may form a bond with -E-, -G-, or -J; or the amine nitrogen of said amino alcohol residue may form a bond with -E-, -G-, or -J, and said alcohol oxygen of said amino alcohol residue may form a bond with -A-, structure I, structure II, structure III, or structure IV.

Non-limiting examples of structures for -E- according to various non-limiting embodiments of the present disclosure include dicarboxylic acid residues or derivatives thereof, as set forth above. In certain non-limiting embodiments of -E-, a first carbonyl group of said dicarboxylic acid residue may form a bond with -G- or -D-, and a second carbonyl group of said dicarboxylic acid residue may form a bond with -G-.

Non-limiting examples of structures for -G- according to various non-limiting embodiments of the present disclosure include polyalkyleneglycol residues and polyol residues and derivatives thereof, as set forth above. In certain non-limiting embodiments where -G- a polyalkyleneglycol residue, non-limiting examples of said polyalkyleneglycol include the structure:

wherein x, y, and z are each a number between 0 and 50, and the sum of x, y, and z is from 1 to 50. In other non-limiting embodiments where -G- is a polyol residue or derivative thereof, a first polyol oxygen of the polyol residue may form a bond with -E-, -D-, structure I, structure II, structure III, or structure IV, and a second polyol oxygen of the polyol may form a bond with -E- or -J.

According to various non-limiting embodiments of the present disclosure, -J comprises the reactive moiety or residue thereof, or alternatively, -J is hydrogen, provided that if -J is hydrogen, -J is bonded to an oxygen of group -D- or -G-, forming a reactive moiety. Non-limiting embodiments of reactive moieties are discussed above.

Further, according to various non-limiting embodiments disclosed herein, one of groups R$_1$, R$_1$', R$_2$, R$_3$, R$_4$, R$_5$, R$_6$, B, and B' on each of structures I, II, III, and IV comprises a reactive substituent R. In another non-limiting embodiment, two of the groups R$_1$, R$_1$', R$_2$, R$_3$, R$_4$, R$_5$, R$_6$, B, and B' on each of structures I, II, III, and IV may comprise a reactive substituent R, wherein the reactive substituents R may be the same or different. In yet another non-limiting embodiment, from 1 and 4 of the groups R$_1$, R$_1$', R$_2$, R$_3$, R$_4$, R$_5$, R$_6$, B, and B' on each of structures I, II, III, and IV may comprise a reactive substituent R, wherein the reactive substituents R may be the same or different.

Non-limiting examples of photochromic materials comprising naphthopyrans comprising a reactive substituent R according to the various embodiments of the present disclosure include the following:

(i) 3,3-di(4-methoxyphenyl)-6-methoxy-7-(3-(2-methacryloxyethyl)carbamyloxymethylenepiperidin-1-yl)-13,13-dimethyl-3H,13H-indeno[2',3':3,4]naphtho[1,2-b]pyran;

(ii) 3-phenyl-3-(4-morpholinophenyl)-6-methoxy-7-(3-(2-methacryloxyethyl)carbamyloxymethylenepiperidin-1-yl)-13,13-dimethyl-3H,13H-indeno[2',3':3,4]naphtho[1,2-b]pyran;

(iii) 3-phenyl-3-(4-(4-phenylpiperazino)phenyl)-6-methoxy-7-(4-(2-methacryloxyethyl)carbamyloxypiperidin-1-yl)-13,13-dimethyl-3H,13H-indeno[2',3':3,4]naphtho[1,2-b]pyran;

(iv) 3-(4-fluorophenyl)-3-(4-methoxyphenyl)-6-methoxy-7-(4-(2-methacryloxyethyl)carbamyloxypiperidin-1-yl)-13,13-dimethyl-3H,13H-indeno[2',3':3,4]naphtho[1,2-b]pyran;

(v) 3-(4-fluorophenyl)-3-(4-morpholinophenyl)-6-methoxy-7-(4-(2-methacryloxyethyl)carbamyloxypiperidin-1-yl)-13,13-dimethyl-3H,13H-indeno[2',3':3,4]naphtho[1,2-b]pyran;
(vi) 3-phenyl-3-(4-morpholinophenyl)-6-methoxy-7-(4-(2-methacryloxyethyl)carbamyloxypiperidin-1-yl)-13,13-dimethyl-3H,13H-indeno[2',3':3,4]naphtho[1,2-b]pyran;
(vii) 3-phenyl-3-(4-morpholinophenyl)-6-methoxy-7-(4-(2-methacryloxyethyl)carbamylpiperazin-1-yl)-13,13-dimethyl-3H,13H-indeno[2',3':3,4]naphtho[1,2-b]pyran;
(viii) 3-phenyl-3-(4-(2-(2-methacryloxyethyl)carbamyloxyethoxy)phenyl)-6-methoxy-7-piperidino-13,13-dimethyl-3H,13H-indeno[2',3':3,4]naphtho[1,2-b]pyran;
(ix) 3-phenyl-3-(4-methoxyphenyl)-6-methoxy-7-(4-(2-methacryloxyethyl)carbamylpiperazin-1-yl)-13,13-dimethyl-3H,13H-indeno[2',3':3,4]naphtho[1,2-b]pyran;
(x) 3-phenyl-3-(4-(2-(2-methacryloxyethyl)carbamyloxyethoxy)phenyl)-6,7-dimethoxy-13,13-dimethyl-3H,13H-indeno[2',3':3,4]naphtho[1,2-b]pyran;
(xi) 3-phenyl-3-(4-(4-(2-methacryloxyethyl)carbamylpiperazin-1-yl)phenyl)-6,11-dimethoxy-13,13-dimethyl-3H,13H-indeno[2',3':3,4]naphtho[1,2-b]pyran;
(xii) 3-phenyl-3-(4-(2-methacryloxyethyl)carbamyloxyphenyl)-6,7-dimethoxy-13,13-dimethyl-3H,13H-indeno[2',3':3,4]naphtho[1,2-b]pyran;
(xiii) 3-phenyl-3-(4-morpholinophenyl)-6-methoxy-7-(3-(2-(2-(2-(2-(2-(2-methacryloxyethoxy)ethoxy)ethoxy)ethoxy)ethoxy)carbonylethyl)carboxymethylenepiperidin-1-yl)-13,13-dimethyl-3H,13H-indeno[2',3':3,4]naphtho[1,2-b]pyran;
(xiv) 3-phenyl-3-(4-methoxyphenyl)-6-methoxy-7-(3-(2-(2-(2-(2-(2-(2-methacryloxyethoxy)ethoxy)ethoxy)ethoxy)ethoxy)carbonylethyl)carboxymethylenepiperidin-1-yl)-13,13-dimethyl-3H,13H-indeno[2',3':3,4]naphtho[1,2-b]pyran;
(xv) 3-phenyl-3-(4-morpholinophenyl)-6-methoxy-7-(4-(2-(2-(2-(2-(2-(2-methacryloxyethoxy)ethoxy)ethoxy)ethoxy)ethoxy)carbonylethyl)carboxypiperidin-1-yl)-13,13-dimethyl-3H,13H-indeno[2',3':3,4]naphtho[1,2-b]pyran;
(xvi) 3-phenyl-3-(4-methoxyphenyl)-6-methoxy-7-(4-(2-(2-(2-(2-(2-(2-methacryloxyethoxy)ethoxy)ethoxy)ethoxy)ethoxy)carbonylethyl)carboxypiperidin-1-yl)-13,13-dimethyl-3H,13H-indeno[2',3':3,4]naphtho[1,2-b]pyran;
(xvii) 3-phenyl-3-(4-(2-(2-(2-(2-(2-(2-(2-methacryloxyethoxy)ethoxy)ethoxy)ethoxy)ethoxy)ethoxy)carbonylethyl)carboxyethoxy)phenyl)-6-methoxy-7-morpholino-13,13-dimethyl-3H,13H-indeno[2',3':3,4]naphtho[1,2-b]pyran;
(xviii) 3-phenyl-3-(4-(4-(2-(2-methacryloxyethyl)carbamyloxyethyl)piperazin-1-yl)phenyl)-13,13-dimethyl-3H,13H-indeno[2',3':3,4]naphtho[1,2-b]pyran;

and mixtures thereof.

Figure 2:
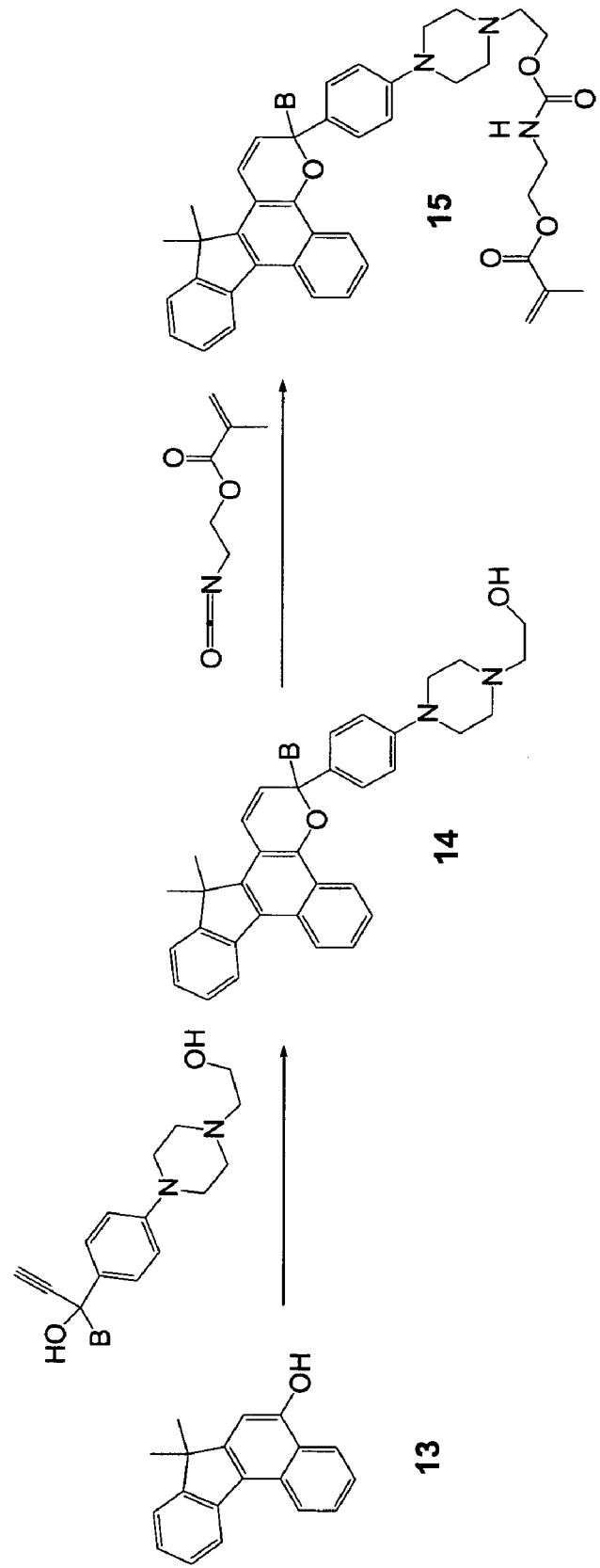

Non-limiting methods of synthesizing the reactive substituent R on the photochromic napthopyran according to various non-limiting embodiments of the photochromic materials comprising a reactive substituent disclosed herein will now be discussed with reference to the reaction schemes presented in FIGS. 1 and 2. FIG. 1 depicts various non-limiting methods of synthesizing a reactive substituent R at the 7 position of an indeno[2',3':3,4]naphtho[1,2-b]pyran. FIG. 2 depicts one non-limiting method of synthesizing a reactive substituent R on a B group of an indeno[2',3':3,4] naphtho[1,2-b]pyran. One skilled in the art will appreciate that there may be multiple ways to synthesize the reactive substituent on the photochromic naphthopyran, therefore it will be appreciated that these reaction schemes are presented for illustration purposes only and are not intended to be limiting herein.

Referring now to FIG. 1, 2,3-dimethoxy-7,7-dimethyl-7H-benzo[C]fluoren-5-ol 5 may be reacted with a substituted 2-propyn-1-ol to form indeno[2',3':3,4]naphtho[1,2-b]pyran 6. Non-limiting methods of synthesizing 7H-benzo[C]fluoren-5-ols, suitable for use in the synthesis of various non-limiting embodiments disclosed herein, are described in U.S. Pat. No. 6,296,785 at col. 11, line 6 to col. 28, line 35, the disclosure of which is incorporated herein by reference. Non-limiting methods of synthesizing substituted 2-propyn-1-ols, suitable for use in the synthesis of various non-limiting embodiments disclosed herein, are described in U.S. Pat. No. 5,458,814 at col. 4, line 11 to col. 5, line 9, and at step 1 of Examples 1, 4-6, 11, 12, and 13, and U.S. Pat. No. 5,645,767 at col. 5, line 12 to col. 6, line 30, the disclosures of which are incorporated herein by reference. Indeno-fused naphthopyran 6 may then be reacted with a diamine or amino alcohol. For example, 6 may be reacted with a diamine, such as piperazine to afford the 6-methoxy-7-(piperizin-1-yl)-13,13-dimethyl-3H,13H-indeno[2',3':3,4]naphtho[1,2-b]pyran 7. The piperazine moiety of 7 may be condensed with 2-iscyanatoethyl methacrylate to afford photochromic naphthopyran 8 having an R substituent comprising -D-J, as defined herein above, where -D- is a diamine residue. Alternatively, indeno-fused naphthopyran 6 may be reacted with an amino alcohol, such as 3-piperidinomethanol to afford the 6-methoxy-7-(3-hydroxymethylenepiperidin-1-yl)-13,13-dimethyl-3H,13H-indeno[2',3':3,4]naphtho[1,2-b]pyran 9. The hydroxy moiety of 9 may be condensed with 2-iscyanatoethyl methacrylate to afford photochromic naphthopyran 10 having an R substituent comprising -D-J, as defined herein above, where -D- is an amino alcohol residue.

Referring still to FIG. 1, the hydroxy moiety of 9 may alternatively be reacted with a cyclic anhydride, such as succinic anhydride to afford the 6-methoxy-7-(3-(2-hydroxycarbonylethylcarboxymethylenepiperidin-1-yl)-13,13-dimethyl-3H,13H-indeno[2',3':3,4]naphtho[1,2-b]pyran 11. The carboxylic acid of 11 may be esterified with polyethyleneglycol methacrylate of afford photochromic naphthopyran 12 having an R substituent comprising -D-E-G-J, as defined herein above.

Referring now to FIG. 2, 7,7-dimethyl-7H-benzo[C]fluoren-5-ol 13 may be reacted with 1-phenyl-1-(4-(4-(2-hydroxyethyl)piperizin-1-yl)phenyl-2-propyn-1-ol, to form indeno[2',3':3,4]naphtho[1,2-b]pyran 14. The hydroxy moiety of 14 may be condensed with 2-iscyanatoethyl methacrylate to afford photochromic naphthopyran 15 having an R substituent on the B group, wherein the reactive substituent R comprises -D-J, as defined herein above, where -D- is an amino alcohol residue.

The photochromic materials of the present disclosure, for example photochromic materials comprising a photochromic naphthopyran and a reactive substituent bonded to the photochromic naphthopyran, wherein the reactive substituent has the structure as set forth herein, may be used in those applications in which photochromic materials may be employed, such as, optical elements, for example, an ophthalmic element, a display element, a window, a mirror, an active liquid crystal cell element, and a passive liquid crystal cell element. As used herein, the term "optical" means pertaining to or associated with light and/or vision. As used herein, the term "ophthalmic" means pertaining to or associated with the eye and vision. As used herein, the term "display" means the visible or machine-readable representation of information in words, numbers, symbols, designs or drawings. Non-limiting examples of display elements include screens, monitors, and security elements, such as security marks. As used herein, the term "window" means an aperture adapted to permit the transmission of radiation therethrough. Non-limiting examples of windows include aircraft and automotive windshields, automotive and aircraft transparencies, e.g., T-roofs, sidelights and backlights, filters, shutters, and optical switches. As used herein, the term "mirror" means a surface that specularly reflects a large fraction of incident light. As used herein, the term "liquid crystal cell" refers to a structure containing a liquid crystal material that is capable of being ordered. One non-limiting example of a liquid crystal cell element is a liquid crystal display In certain non-limiting embodiments, the photochromic materials of the present disclosure may be used in an ophthalmic element, such as, corrective lenses, including single vision or multi-vision lenses, which may be either segmented or non-segmented multi-vision lenses (such as, but not limited to, bifocal lenses, trifocal lenses and progressive lenses), non-corrective lenses, a magnifying lens, a protective lens, a visor, goggles, and a lens for an optical instrument, such as a camera or telescope lens. In other non-limiting embodiments, the photochromic materials of the present disclosure may be used in plastic films and sheets, textiles, and coatings.

The photochromic materials according to various non-limiting embodiments disclosed herein may be incorporated into an organic material, such as a polymeric, oligomeric, or monomeric material, which may be used, for example and without limitation, to form articles of manufacture, such as optical elements, and coatings that can be applied to other substrates. As used herein the term "incorporated into" means physically and/or chemically combined with. Thus, the photochromic materials according to various non-limiting embodiments disclosed herein may be physically and/or chemically combined with at least a portion of an organic material. As used herein the terms "polymer" and "polymeric material" refers to homopolymers and copolymers (e.g., random copolymers, block copolymers, and alternating copolymers), as well as blends and other combinations thereof. Further, it is contemplated that the photochromic materials according to various non-limiting embodiments disclosed herein may each be used alone, in combination with other photochromic materials according to various non-limiting embodiments disclosed herein, or in combination with other appropriate complementary conventional photochromic materials. For example, the photochromic materials according to various non-limiting embodiments disclosed herein may be used in conjunction with other complementary conventional photochromic materials having an activated absorption maxima within the range of 300 to 1000 nanometers. The complementary conventional photochromic materials may include other polymerizable or compatabilized photochromic materials.

The present disclosure also contemplates photochromic compositions comprising a polymeric material and a photochromic material according to the various non-limiting embodiments discussed herein. As used herein, the term "photochromic composition" refers to a photochromic material in combination with another material, which may or may not be a photochromic material. In certain non-limiting examples of the photochromic compositions according to various non-limiting embodiments of the present disclosure, the photochromic material is incorporated into at least a portion of the polymeric material. For example, and without limitation, the photochromic materials disclosed herein may be incorporated into a portion of the polymeric material, such as by bonding to a portion of the polymeric material, for example by co-polymerizing the photochromic material with a portion of the polymeric material; or blending with the polymeric material. As used herein, the term "blended" or "blending" mean that the photochromic material is intermixed or intermingled with at least a portion of an organic material, such as the polymeric material, but not bonded to the organic material. As used herein, the terms "bonded" or "bonding" mean that the photochromic material is linked to a portion of an organic material, such as the polymeric material, or a precursor thereof. For example, in certain non-limiting embodiments, the photochromic material may be bonded to a portion of an organic material through a reactive substituent (such, but not limited to, those reactive substituents discussed above).

According to one non-limiting embodiment wherein the organic material is a polymeric material, the photochromic material may be incorporated into at least a portion of the polymeric material or at least a portion of the monomeric material or oligomeric material fro which the polymeric material is formed. For example, photochromic materials according to various non-limiting embodiments disclosed herein that have a reactive substituent may be bonded to an organic material such as a monomer, oligomer, or polymer having a group with which a reactive moiety may be reacted, or the reactive moiety can be reacted as a co-monomer in the polymerization reaction from which the organic material is formed, for example, in a co-polymerization process. As used, herein, the term "co-polymerized with" means that the photochromic material is linked to a portion of the polymeric material by reacting as a co-monomer in the polymerization reaction of the host monomers that result in the polymeric material. For example, photochromic materials according to various non-limiting embodiments herein that have a reactive substituent that comprises a polymerizable moiety may react as a co-monomer during the polymerization of the host monomers.

Polymeric materials suitable for the various non-limiting embodiments of the present disclosure includes, but is not limited to polyacrylates, polymethacrylates, poly($C_1$-$C_{12}$) alkylated methacrylates, polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly((meth)acrylic acid), thermoplastic polycarbonates, polyesters, polyurethanes, polythiourethanes, poly(ethylene terephthalate), polystyrene, poly(alpha-methylstyrene), copoly(styrene-methylmethacrylate), copoly(styrene-acrylonitrile), polyvinylbutyral, and polymers of members of the group consisting of polyol(allyl carbonate) monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers, and diallyidene pentaerythritol monomers. In certain non-limiting embodiments of the photochromic compositions of the present disclosure, the polymeric material comprises a homopolymer or a copolymer of monomer(s) chosen from acrylates, methacrylates, methyl methacrylate, ethylene glycol bis methacrylate, thoxylated bisphenol A dimethacrylate, vinyl acetate, vinylbutyral, urethane, thiourethane, diethylene glycol, bis(allyl carbonate), diethylene glycol dimethacrylate, diisopropenyl benzene, ethoxylated trimethylol propane triacrylate, and combinations thereof.

Transparent copolymers and blends of transparent polymers are also suitable host polymeric materials for the photochromic compositions according to the various non-limiting embodiments disclosed herein. For example, according to various non-limiting embodiments, the polymeric material may be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; polymerizates of a polyol(allyl carbonate)monomer, especially diethylene glycol bis(allyl carbonate), which monomer is sold under the trademark CR-39®; and polyurea-polyurethane(polyurea urethane)polymers, which are prepared, for example, by the reaction of a polyurethane prepolymer and a diamine curing agent, a composition for one such polymer being sold under the trademark TRIVEX® by PPG Industries, Inc (Pittsburgh, Pa., USA). Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate; copolymers with a polyurethane having terminal diacrylate functionality; and copolymers with aliphatic urethanes, the terminal portion of which contain allyl or acryloyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol)bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate, acrylonitrile, and combinations thereof. According to one non-limiting embodiment, the polymeric material may be an optical resin sold by PPG Industries, Inc. under the CR-designation, e.g., CR-307, CR-407, and CR-607.

Various non-limiting embodiments disclosed herein provide photochromic articles comprising a substrate and a photochromic material according to any of the non-limiting embodiments discussed above connected to a portion of the substrate. As used herein, the term "connected to" means associated with, either directly or indirectly through another material or structure. In one non-limiting embodiment, the photochromic articles of the present disclosure may be an optical element, for example, but not limited to, an ophthalmic element, a display element, a window, a mirror, an active liquid crystal cell element, and a passive liquid crystal cell element. In certain non-limiting embodiments, the photochromic article is an ophthalmic element, for example, but not limited to, corrective lenses, including single vision or multi-vision lenses, which may be either segmented or non-segmented multi-vision lenses (such as, but not limited to, bifocal lenses, trifocal lenses and progressive lenses), non-corrective lenses, a magnifying lens, a protective lens, a visor, goggles, and a lens for an optical instrument.

For example and without limitation, the photochromic materials disclosed herein may be connected to at least a portion of the substrate, such as by bonding the photochromic materials to at least a portion of the material from which the substrate is made, for example by co-polymerizing or otherwise bonding the photochromic materials with the substrate material; blending the photochromic materials with the substrate material; or coating the photochromic materials on at least a portion of a surface of the substrate. Alternatively, with the photochromic material may be connected to at least a portion of the substrate such as through an intermediate coating, film or layer.

According to various non-limiting embodiments disclosed herein wherein the substrate of the photochromic article comprises a polymeric material, the photochromic material may be connected to at least a portion of the substrate by incorporating the photochromic material into at least a portion of the polymeric material of the substrate, or at least a portion of the oligomeric or monomeric material from which the substrate is formed. For example, according to one non-limiting embodiment, the photochromic material may be incorporated into the polymeric material of the substrate by the cast-in-place method. Additionally or alternatively, the photochromic material may be connected with at least a portion of the polymeric material of the substrate by imbibition. Imbibition and the cast-in-place method are discussed below.

For example, according to one non-limiting embodiment, the substrate comprises a polymeric material and a photochromic material is bonded to at least a portion of the polymeric material. According to another non-limiting embodiment, the substrate comprises a polymeric material and a photochromic material is blended with at least a portion of the polymeric material. According to another non-limiting embodiment, the substrate comprises a polymeric material and a photochromic material is co-polymerized with at least a portion of the polymeric material. Non-limiting examples of polymeric materials that are useful in forming the substrates according to various non-limiting embodiments disclosed herein are set forth above in detail.

According to other non-limiting embodiments, the photochromic material may be connected to at least a portion of the substrate of the photochromic article as part of an at least partial coating that is connected to at least a portion of a substrate. According to this non-limiting embodiment, the substrate may be a polymeric substrate or an inorganic substrate (such as, but not limited to, a glass substrate). Further, the photochromic material may be incorporated into at least a portion of the coating composition prior to application of the coating composition to the substrate, or alternatively, a coating composition may be applied to the substrate, at least partially set, and thereafter the photochromic material may be imbibed into at least a portion of the coating. As used herein, the terms "set" and "setting" include, without limitation, curing, polymerizing, cross-linking, cooling, and drying.

For example, in one non-limiting embodiment of the present disclosure, the photochromic article may comprise an at least partial coating of a polymeric material connected to at least a portion of a surface thereof. According to this non-limiting embodiment, the photochromic material may be blended with at least a portion of the polymeric material of the at least partial coating, or the photochromic material may be bonded to at least a portion of the polymeric material of the at least partial coating. According to one specific non-limiting embodiment, the photochromic material may be co-polymerized with at least a portion of the polymeric material of the at least partial coating.

The at least partial coating comprising a photochromic material may be directly connected the substrate, for example, by directly applying a coating composition comprising a photochromic material to at least a portion of a surface of the substrate, and at least partially setting the coating composition. Additionally or alternatively, the at least partial coating comprising a photochromic material may be connected to the substrate, for example, through one or more additional coatings. For example, while not limiting herein, according to various non-limiting embodiments, an additional coating composition may be applied to at least a portion of the surface of the substrate, at least partially set, and thereafter the coating composition comprising a photochromic material may be applied over the additional coating and at least partially set.

Non-limiting examples of additional coatings and films that may be used in conjunction with the optical elements disclosed herein include primer coatings and films; protective coatings and films, including transitional coatings and films and abrasion resistant coatings and films; anti-reflective coatings and films; conventional photochromic coating and films; polarizing coatings and films; and combinations thereof. As used herein, the term "protective coating or film" refers to coatings or films that may prevent wear or abrasion, provide a transition in properties from one coating or film to another, protect against the effects of polymerization reaction chemicals and/or protect against deterioration due to environmental conditions, such as moisture, heat, ultraviolet light, oxygen, etc.

Non-limiting examples of primer coatings and films that may be used in conjunction with various non-limiting embodiments disclosed herein include coatings and films comprising coupling agents, partial hydrolysates of coupling agents, and mixtures thereof. As used herein, the term "coupling agent" means a material having a group capable of reacting, binding and/or associating with a group on one or more surfaces. In one non-limiting embodiment, a coupling agent may serve as a molecular bridge at the interface of two or more surfaces that may be similar or dissimilar surfaces. Coupling agents, in another non-limiting embodiment, may be monomers, oligomers, and/or polymers. Such materials include, but are not limited to, organo-metallics such as silanes, titanates, zirconates, aluminates, zirconium aluminates, hydrolysates thereof and mixtures thereof. As used herein, the phrase "partial hydrolysates of coupling agents" means that some to all of the hydrolyzable groups on the coupling agent are hydrolyzed.

As used herein, the term "transitional coating and film" means a coating or film that aids in creating a gradient in properties between two coatings or films, or a coating and a film. For example, although not limiting herein, a transitional coating may aid in creating a gradient in hardness between a relatively hard coating and a relatively soft coating.

As used herein, the term "abrasion resistant coating and film" refers to a coating of a protective polymeric material that demonstrates a resistance to abrasion that is greater than a standard reference material, e.g., a polymer made of CR-39® monomer available from PPG Industries, Inc., as tested in a method comparable to ASTM F-735 Standard Test Method for Abrasion Resistance of Transparent Plastics and Coatings Using the Oscillating Sand Method. Non-limiting examples of abrasion resistant coatings include abrasion-resistant coatings comprising organosilanes, organosiloxanes, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof.

Non-limiting examples of antireflective coatings and films include a monolayer, multilayer or film of metal oxides, metal fluorides, or other such materials, which may be deposited onto the articles disclosed herein or a film, for example, through vacuum deposition, sputtering, or some other method. Non-limiting examples of conventional photochromic coatings and films include, but are not limited to, coatings and films comprising conventional photochromic materials. Non-limiting examples of polarizing coatings and films include, but are not limited to, coatings and films comprising dichroic compounds that are known in the art.

As discussed above, according to various non-limiting embodiments, these coatings and films may be applied to the substrate prior to applying the at least partial coating comprising a photochromic material according to various non-limiting embodiments disclosed herein. Alternatively or additionally, these coatings may be applied to the substrate after applying the at least partial coating comprising a photochromic material, for example as an overcoating on the at least partial coating comprising a photochromic material. For example, while not limiting herein, according to various other non-limiting embodiments, the aforementioned coatings may be connected to at least a portion of the same surface of a substrate in the following order from the surface: primer, photochromic, transitional, abrasion resistant, polarizing film or coating, antireflective, and abrasion resistant; primer, photochromic, transitional, abrasion resistant, and antireflective; or photochromic, transitional, and polarizing; or primer, photochromic, and polarizing; or primer, photochromic, and antireflective. Further, the aforementioned coating may be applied to both surfaces of the substrate.

The present disclosure also contemplates various methods of making photochromic articles comprising connecting a photochromic material, according to the various non-limiting embodiments disclosed herein, to at least a portion of a substrate. For example, in one non-limiting embodiment wherein the substrate comprises a polymeric material, connecting the photochromic material to at least a portion of the substrate may comprise blending the photochromic material with at least a portion of the polymeric material of the substrate. In another non-limiting embodiment, connecting the photochromic material to at least a portion of the substrate may comprise bonding the photochromic material to at least a portion of the polymeric material of the substrate. For example, in one non-limiting embodiment, connecting the photochromic material to at least a portion of the substrate may comprise co-polymerizing the photochromic material with at least a portion of the polymeric material of the substrate. Non-limiting methods of connecting photochromic materials to a polymeric material include, for example, mixing the photochromic material into a solution or melt of a polymeric, oligomeric, or monomeric material, and subsequently at least partially setting the polymeric, oligomeric, or monomeric material. It will be appreciated by those skilled in the art that, according to this non-limiting embodiment, in the resultant photochromic composition, the photochromic materials may be blended with the polymeric material (i.e., intermixed with but not bonded to) or bonded to the polymeric material. For example, if the photochromic material contains a polymerizable group that is compatible with the polymeric, oligomeric, or monomer material, during setting of the organic material the photochromic material can be reacted with at least a portion thereof to bond the photochromic material thereto.

In another non-limiting embodiment, connecting the photochromic material to at least a portion of the substrate may comprise imbibing the photochromic material with at least a portion of the polymeric material of the substrate. According to this non-limiting embodiment, the photochromic material may be caused to diffuse into the material, for example, by immersing a polymeric material in a solution containing the photochromic material, with or with out heating. Thereafter, the photochromic material may be bonded to the polymeric material as discussed above. In another non-limiting embodiment, the connecting the photochromic material to at least a portion of the substrate may comprise a combination of two or more of blending, bonding (for example co-polymerizing), and imbibing the photochromic material to/with at least a portion of the polymeric material of the substrate.

According to one non-limiting embodiment, wherein the substrate comprises a polymeric material, incorporating the photochromic material with at least a portion of a substrate comprises a cast-in-place method. According to this non-limiting embodiment, the photochromic material may be mixed with a polymeric solution or melt, or other oligomeric and/or monomeric solution or mixture, which is subsequently cast into a molding having a desired shape and at least partially set to form the substrate. Further, although not required according to this non-limiting embodiment, a photochromic material can be bonded to the polymeric material.

According to another non-limiting embodiment, wherein the substrate comprises a polymeric material, connecting the photochromic material to at least a portion of a substrate comprises in-mold casting. According to this non-limiting embodiment, a coating composition comprising the photochromic material, which may be a liquid coating composition or a powder coating composition, is applied to the surface of a mold and at least partially set. Thereafter, a polymer solution or melt, or oligomer or monomeric solution or mixture is cast over the coating and at least partially set. After setting, the substrate with the coating is removed from the mold.

According to still another non-limiting embodiment, wherein the substrate comprises a polymeric material or an inorganic material such as glass, connecting the photochromic material to at least a portion of a substrate comprises applying an at least partial coating or lamination comprising the photochromic material to at least a portion of the substrate. Non-limiting examples of suitable coating methods include spin coating, spray coating (e.g., using a liquid or powder coating), curtain coating, roll coating, spin and spray coating, and over-molding. For example, according to one non-limiting embodiment, the photochromic material may be connected to the substrate by over-molding. According to this non-limiting embodiment, a coating composition comprising the photochromic material (which may be a liquid coating composition or a powder coating composition as previously discussed) is applied to a mold and the substrate is then placed into the mold such that the substrate contacts the coating causing it to spread over at least a portion of the surface of the substrate. Thereafter, the coating composition is at least partially set and the coated substrate is removed from the mold. Alternatively, over-molding may be done by placing the substrate into a mold such that an open region is defined between the substrate and the mold, and thereafter injecting a coating composition comprising the photochromic material into the open region. Thereafter, the coating composition can be at least partially set and the coated substrate is removed from the mold.

According to yet another non-limiting embodiment, a film comprising the photochromic material may be adhered to a portion of the substrate, with or without an adhesive and/or the application of heat and pressure. Thereafter, if desired, a second substrate may be applied over the first substrate and the two substrates may be laminated together (i.e., by the application of heat and pressure) to form an element wherein the film comprising the photochromic material is interposed between the two substrates. Methods of forming films comprising a photochromic material may include, for example and without limitation, combining a photochromic material with a polymeric solution or oligomeric solution or mixture, casting or extruding a film therefrom, and, if required, at least partially setting the film. Additionally or alternatively, a film may be formed (with or without a photochromic material) and imbibed with the photochromic material (as discussed above).

Further, it will be appreciated by those skilled in the art that the photochromic compositions, photochromic articles, and photochromic coating compositions according to various non-limiting embodiments disclosed herein may further comprise other additives that aid in the processing and/or performance of the composition. For example, and without limitation, such additives may include complementary photochromic materials, photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, or adhesion promoters (such as hexanediol diacrylate and coupling agents).

Each of the photochromic materials described herein may be used in amounts (or in a ratio) such that a substrate or a polymeric material to which the photochromic material is associated, i.e., blended, co-polymerized or otherwise bonded, coated and/or imbibed, exhibits a desired resultant color, e.g., substantially clear and colorless when the photochromic material is in the closed form and substantially colored when activated by actinic radiation and the photochromic material is in the open form.

The amount of the photochromic naphthopyrans of the present disclosure to be connected to or incorporated into a coating composition, polymeric material, substrate, photochromic composition, and/or photochromic articles is not critical provided that a sufficient amount is used to produce the desired optical effect. Generally, such amount may be described as a "photochromic amount". The particular amount of photochromic material used may depend on a variety of factors such as, the absorption characteristics of the photochromic material used, the intensity of color desired upon irradiation thereof, and the method used to incorporate or apply the photochromic material.

The relative amounts of the aforesaid photochromic materials used in the various methods of the non-limiting embodiments of the present disclosure will vary and depend, in part, upon the relative intensities of the color of the activated species of such materials, the ultimate color desired, the molar absorption coefficient (of "extinction coefficient") for actinic radiation, and the method of application to the polymeric material or substrate. Generally, the amount of total photochromic material incorporated into or connected to a polymeric material or substrate may range from about 0.05 to about 5.0 milligrams per square centimeter of the surface to which the photochromic material is incorporated into or connected to. The amount of photochromic material incorporated into or connected to a coating composition may range from 0.1 to 40 weight percent based on the weight of the liquid coating composition. The amount of photochromic material incorporated into, i.e., blended with, co-polymerized with, or bonded to, a host polymer photochromic composition or photochromic article, such as by a in cast-in-place type method, may range from 0.01 to 40 weight percent based on the weight of the polymeric composition or photochromic article.

EXAMPLES

The following examples illustrate various non-limiting embodiments of the compositions and methods within the present disclosure and are not restrictive of the invention as otherwise described herein.

Example 1

Step 1

2,3-Dimethoxy-7,7-dimethyl-7H-benzo[C]fluoren-5-ol (10 g), 1-phenyl-1-(4-morpholinophenyl)-2-propyn-1-ol (13 g), dodecyl benzenesulfonic acid (10 drops), and chloroform (400 mL) were combined in a reaction flask. The reaction mixture was heated at reflux for 3 hours and concentrated. Acetone was added to the residue, and the slurry was filtered, yielding 18 g of off-white solid.

Step 2

3-Phenyl-3-(4-morpholinophenyl)-6,7-dimethoxy-13,13-dimethyl-3H,13H-indeno[2',3':3,4]naphtho[1,2-b]pyran from Step 1 (20 g), 3-piperidinomethanol (7.6 g), and tetrahydrofuran (250 mL) were combined in a dry reaction flask cooled with ice bath under nitrogen atmosphere. Butyl lithium in hexane (2.5 M, 50 mL) was added to the reaction mixture dropwise under stirring. The cooling bath was removed after the addition and the flask was warmed to room temperature. The dark solution was poured into ice water (400 mL) and the mixture was extracted with ethyl acetate (twice with 400 mL). The organic layer was washed with saturated sodium chloride aqueous solution (200 mL), dried over sodium sulfate and concentrated. The residue was purified by silica gel chromatography (ethyl acetate/hexanes (v/v): 1/1.5). The product was obtained as an expanded brown-tinted foam (17 g).

Step 3

3-Phenyl-3-(4-morpholinophenyl)-6-methoxy-7-(3-hydroxymethylenepiperidin-1-yl)-13,13-dimethyl-3H,13H-indeno[2',3':3,4]naphtho[1,2-b]pyran from Step 2 from Step 1 (9 g), 2-isocyanatoethyl methacrylate (3 mL), dibutyltin laureate (5 drops) and ethyl acetate (200 mL) were combined in a reaction flask with a condenser open to air. The mixture was heated at reflux for 30 minutes. Methanol (15 mL) was added to the mixture to quench excess 2-isocyanatoethyl methacrylate. The reaction mixture was concentrated and the residue was purified by silica gel chromatography (ethyl acetate/hexanes (v/v): 1/1). The product was obtained as an expanded purple-tinted foam (11 g). Nuclear magnetic resonance spectroscopy ("NMR") supports the structure of 3-phenyl-3-(4-morpholinophenyl)-6-methoxy-7-(3-(2-methacryloxyethyl) carbamyloxymethylenepiperidin-1-yl)-13,13-dimethyl-3H, 13H-indeno[2',3':3,4]naphtho[1,2-b]pyran.

Example 2

Step 1

The procedure of Step 2 of Example 1 was followed except that 4-hydroxypiperidine was used in place of 3-piperidinomethanol. The product was obtained as off-white crystals.

Step 2

The procedure of Step 3 of Example 1 was followed except that 3-phenyl-3-(4-morphlinophenyl)-6-methoxy-7-(4-hydroxypiperidin-1-yl)-13,13-dimethyl-3H,13H-indeno[2',3': 3,4]naphtho[1,2-b]pyran (from Step 1) was used in place of 3-phenyl-3-(4-morpholinophenyl)-6-methoxy-7-(3-hydroxymethylenepiperidin-1-yl)-13,13-dimethyl-3H,13H-indeno[2',3':3,4]naphtho[1,2-b]pyran. The product was obtained as purple-tinted crystals. Mass spectrometry supports the molecular weight of 3-phenyl-3-(4-morphlinophenyl)-6-methoxy-7-(4-(2-methacryloxyethyl)carbamyloxypiperidin-1-yl)-13,13-dimethyl-3H,13H-indeno[2',3':3,4] naphtho[1,2-b]pyran.

Example 3

Step 1

The procedure of Step 2 of Example 1 was followed except that piperazine was used in place of 3-piperidinomethanol. The product was obtained as purple-tinted crystals.

Step 2

3-Phenyl-3-(4-morpholinophenyl)-6-methoxy-7-(4-piperazin-1-yl)-13,13-dimethyl-3H,13H-indeno[2',3':3,4]naphtho[1,2-b]pyran from Step 1 (10 g), 2-isocyanatoethyl methacrylate (3 mL) and ethyl acetate (150 mL) were combined in a dry reaction flask open to air. The mixture was stirred at room temperature for 20 minutes. Methanol (5 mL) was added to the mixture to quench excess 2-isocyanatoethyl methacrylate. The mixture was concentrated and the residue was purified by silica gel chromatography (ethyl acetate/hexanes (v/v): 1/1). After the chromatography, the product was crystallized from ethyl acetate/hexanes (v/v: 1/1) and filtered off as purple-tinted crystals (10 g). Mass spectrometry supports the molecular weight of 3-phenyl-3-(4-morpholinophenyl)-6-methoxy-7-(4-(2-methacryloxyethyl)carbamylpiperazin-1-yl)-13,13-dimethyl-3H,13H-indeno[2',3':3,4] naphtho[1,2-b]pyran.

Example 4

Step 1

4-Hydroxybenzophenone (100 g), 2-chloroethanol (50 g), sodium hydroxide (20 g) and water (500 mL) were combined in a reaction flask. The mixture was heated at reflux for 6 hours. The oily layer was separated and crystallized upon cooling, the crystals were washed with aqueous sodium hydroxide followed by water and dried, yielding 85 g of off-white solid. The product was used without further purification.

Step 2

4-(2-Hydroxyethoxy)benzophenone from Step 1 (30 g) was dissolved in anhydrous dimethylformamide (250 mL) in a reaction flask with overhead stirring. Sodium acetylide paste (15 g) in toluene was added to the reaction flask under vigorous stirring. After the reaction was complete, the mixture was added to water (500 mL), and the solution was extracted with ethyl ether (twice with 500 mL). The organic layers were combined and washed with saturated aqueous sodium chloride solution and dried over sodium sulfate. The solution was then filtered and concentrated, and the dark residue was purified by silica gel chromatography (ethyl acetate/hexanes (v/v): 1/1). The product was obtained as a white solid (33 g).

Step 3

The procedure of Step 1 of Example 1 was followed except that 1-phenyl-1-(4-(2-hydroxyethoxy)phenyl)-2-propyn-1-ol (from Step 2) was used in place of 1-phenyl-1-(4-morpholinophenyl)-2-propyn-1-ol. After the chromatography, the product was precipitated from ethyl acetate/hexanes (v/v: 1/1) and filtered off as a yellow-tinted solid.

Step 4

The procedure of Step 2 of Example 1 was followed except that 3-phenyl-3-(4-(2-hydroxyethoxy)phenyl)-6,7-dimethoxy-13,13-dimethyl-3H,13H-indeno[2',3':3,4]naphtho[1,2-b]pyran (from Step 3) was used in place of 3-phenyl-3-(4-morpholinophenyl)-6,7-dimethoxy-13,13-dimethyl- 3H,13H-indeno[2',3':3,4]naphtho[1,2-b]pyran and piperidine was used in place of 3-piperidinomethanol. The product was obtained as a dark-green expanded foam.

Step 5

The procedure of Step 3 of Example 1 was followed except that 3-phenyl-3-(4-(2-hydroxyethoxy)phenyl)-6-methoxy-7-piperidino-13,13-dimethyl-3H,13H-indeno[2',3':3,4]naphtho[1,2-b]pyran (from Step 4) was used in place of 3-phenyl-3-(4-morpholinophenyl)-6-methoxy-7-(3-hydroxymethylenepiperidin-1-yl)-13,13-dimethyl-3H,13H-indeno[2',3':3,4]naphtho[1,2-b]pyran. The product was obtained as a yellow-tinted expanded foam. Mass spectrometry supports the molecular weight of 3-phenyl-3-(4-(2-(2-methacryloxyethyl) carbamyloxyethoxy)phenyl)-6-methoxy-7-piperidino-13,13-dimethyl-3H,13H-indeno[2',3':3,4] naphtho[1,2-b]pyran.

Example 5

Step 1

4-Fluorobenzophenone (30 g), piperazine (23 g), triethyl amine (23 mL), potassium carbonate (22 g) and dimethyl sulfoxide (50 mL) were combined into a reaction flask, the mixture was heated at reflux for 20 hours. After this time, the mixture was cooled and poured into water, the slurry was extracted with chloroform and the chloroform phase was washed with water twice and dried over sodium sulfate. The solution was concentrated to 45 g of orange oil. The product was used without further purification.

Step 2

4-Piperazinobenzophenone from Step 1 was dissolved in dimethylformamide (50 mL) in a reaction flask, excess amount of sodium acetylide (9 wt % in toluene) was added portion-wise. After the reaction was complete, the mixture was poured into water, the mixture was then extracted with ethyl acetate, and the organic layer was dried over sodium sulfate. The solution was filtered and concentrated. The residue was purified by silica gel chromatography (ethyl acetate/methanol (v/v): 1/1), yielding 17 g of a yellow solid.

Step 3

The procedure of Step 1 of Example 1 was followed except that 3,9-dimethoxy-7,7-dimethyl-7H-benzo[C]-fluoren-5-ol was used in place of 2,3-dimethoxy-7,7-dimethyl-7H-benzo[C]-fluoren-5-ol and 1-phenyl-1-(4-piperazinophenyl)-2-propyn-1-ol (from step 2) was used in place of 1-phenyl-1-(4-morpholinophenyl)-2-propyn-1-ol. After the chromatography, the product was precipitated from acetone/methanol (v/v: 1/1) and filtered off as a green-tinted solid.

Step 4

Phenyl-3-(4-piperazinophenyl)-6,11-dimethoxy-13,13-dimethyl-3H,13H-indeno[2',3':3,4]naphtho[1,2-b]pyran from Step 3 (1 g), 2-isocyanatoethyl methacrylate (1.5 mL) and ethyl acetate (30 mL) were combined in a dry reaction flask. The mixture was stirred at room temperature for 1 hour. Methanol (5 mL) was added to the mixture to quench excess 2-isocyanatoethyl methacrylate. The mixture was concentrated and the residue was purified by silica gel chromatography (ethyl acetate/hexanes (v/v): 1/1). The product was obtained as a green expanded foam. Mass spectrometry supports the molecular weight of 3-phenyl-3-(4-(4-(2-methacryloxyethyl)carbamylpiperazin-1-yl)phenyl)-6,11-dimethoxy-13,13-dimethyl-3H,13H-indeno[2',3':3,4]naphtho[1,2-b]pyran.

Example 6

Step 1

4-Fluorobenzophenone (20 g) and 1-(2-hydroxyethyl)piperazine (40 g) were heated to 160° C. in 200 ml of DMSO for 3 hours. The mixture was poured into water (1 L) and the solid collected by filtration. The solid was washed with water, dried, slurred in hexane, and dried again. The off-white solid (25 g) was used in the next step without further purification.

Step 2

4-(4-(2-Hydroxyethyl)piperazin-1-yl)-benzophenone from Step 1 (25 g) was dissolved in dimethylformamide (50 mL) in a reaction flask and excess amount of sodium acetylide (9 wt % in toluene) was added portion-wise. After the reaction was complete, the mixture was poured into water, and 20 g of white solid was filtered off.

Step 3

The procedure of Step 2 of Example 1 was followed except that 7,7-dimethyl-7H-benzo[C]fluoren-5-ol was used in place of 2,3-dimethoxy-7,7-dimethyl-7H-benzo[C]fluoren-5-ol and 1-phenyl-1-(4-(4-(2-hydroxyethylpiperazin-1-yl)phenyl)-2-propyn-1-ol (from Step 2) was used in place of 1-phenyl-1-(4-morpholinophenyl)-2-propyn-1-ol. The product was isolated by column chromatography, eluting with ethyl acetate/methanol 80/20 (v/v), and crystallized from methanol as an off-white solid.

Step 4

The procedure of Step 3 of Example 1 was followed except that 3-phenyl-3-(4-(4-(2-hydroxyethyl)piperazin-1-yl)phenyl)-13,13-dimethyl-3H,13H-indeno[2',3':3,4]naphtho[1,2-b]pyran (from Step 3) was used in place of 3-phenyl-3-(4-morpholinophenyl)-6-methoxy-7-(3-hydroxymethylenepiperidin-1-yl)-13,13-dimethyl-3H,13H-indeno[2',3':3,4]naphtho[1,2-b]pyran. Successive chromatographic separations with chloroform/methanol 90/10 (v/v), and with ethyl acetate/methanol 95/5 (v/v), yielded a pure oil that was isolated as a purple-tinted expanded foam. Mass spectrometry supports the molecular weight of 3-phenyl-3-(4-(4-(2-(2-methacryloxyethyl)carbamyloxyethyl)piperazin-1-yl)phenyl)-13,13-dimethyl-3H,13H-indeno[2',3':3,4]naphtho[1,2-b]pyran.

Example 7

Step 1

The procedure of Step 1 of Example 1 was followed except that 1-phenyl-1-(4-methoxyphenyl)-2-propyn-1-ol was used in place of 1-phenyl-1-(4-morpholinophenyl)-2-propyn-1-ol. The product was obtained as off-white crystals.

Step 2

The procedure of Step 2 of Example 1 was followed except that 3-phenyl-3-(4-methoxyphenyl)-6,7-dimethoxy-13,13-dimethyl-3H,13H-indeno[2',3':3,4]naphtho[1,2-b]pyran (from Step 1) was used in place of 3-phenyl-3-(4-morpholinophenyl)-6,7-dimethoxy-13,13-dimethyl-3H,13H-indeno[2',3':3,4]naphtho[1,2-b]pyran and 4-hydroxypiperidine was used in place of 3-piperidinomethanol. After the chromatography, the product was crystallized from ethyl ether/methanol/hexanes (1/1/1), yielding yellow-tinted crystals.

Step 3

3-Phenyl-3-(4-methoxyphenyl)-6-methoxy-7-(4-hydroxypiperidin-1-yl)-13,13-dimethyl-3H,13H-indeno[2',3':3,4]naphtho[1,2-b]pyran from Step 2 (1 g), succinic anhydride (0.3 g), triethyl amine (0.5 mL) and toluene (20 mL) were combined in a dry reaction flask. The mixture was heated at reflux for 7 hours. Water (50 mL) was added to the solution and the mixture was partitioned. The toluene layer was washed with saturated sodium chloride aqueous solution and dried over sodium sulfate. The solution was concentrated and the residue was purified by silica gel chromatography (ethyl acetate/hexanes (v/v): 2/1), yielding 1.2 g of an expanded yellow-tinted foam.

Step 4

3-Phenyl-3-(4-methoxyphenyl)-6-methoxy-7-(4-(2-hydroxycarbonylethyl)carboxypiperidin-1-yl)-13,13-dimethyl-3H,13H-indeno[2',3':3,4]naphtho[1,2-b]pyran from Step 3 (1.2 g), poly(ethylene glycol)methacrylate (average molecular weight 360, 1 mL), dicyclohexyl carbodiimide (0.7 g), 4-(dimethylamino)-pyridine (0.4 g) and methylene chloride (10 mL) were combined in a dry reaction flask. The mixture was heated at reflux for 5 hours and filtered. The solution was concentrated and the residue was purified by silica gel cromatography (ethyl acetate/hexanes (v/v): 1/1), yielding 1.8 g of oily mixture. MS indicates the major components have 5 to 8 ethoxy groups in the polyethylene glycol chain including the compound 3-phenyl-3-(4-methoxyphenyl)-6-methoxy-7-(4-(2-(2-(2-(2-(2-(2-(2-methacryloxyethoxy)ethoxy)ethoxy)ethoxy)ethoxy)carbonylethyl)carboxypiperidin-1-yl)-13,13-dimethyl-3H,13H-indeno[2',3':3,4]naphtho[1,2-b]pyran.

Example 8

Step 1

The procedure of Step 3 of Example 7 was followed except that 3-phenyl-3-(4-morpholinophenyl)-6-methoxy-7-(4-(3-hydroxymethylenepiperidin)-1-yl)-13,13-dimethyl-3H,13H-indeno[2',3':3,4]naphtho[1,2-b]pyran (from Step 2 of Example 1) was used in place of 3-phenyl-3-(4-methoxyphenyl)-6-methoxy-7-(4-hydroxypiperidin-1-yl)-13,13-dimethyl-3H,13H-indeno[2',3':3,4]naphtho[1,2-b]pyran. The product was obtained as a purple-tinted expanded foam.

Step 2

The procedure of Step 4 of Example 7 was followed except that 3-phenyl-3-(4-morpholinophenyl)-6-methoxy-7-(4-(2-hydroxycarbonylethyl)carboxymethylenepiperidin-1-yl)-13,13-dimethyl-3H,13H-indeno[2',3':3,4]naphtho[1,2-b]pyran (from Step 1) was used in place of 3-phenyl-3-(4-methoxyphenyl)-6-methoxy-7-(4-(2-hydroxycarbonylethyl)carboxypiperidin-1-yl)-13,13-dimethyl-3H,13H-indeno[2',3':3,4]naphtho[1,2-b]pyran. The product was obtained as an oily mixture. Mass spectrometry indicates the major component is with 5 to 8 ethoxy groups in the ethylene glycol chain including 3-phenyl-3-(4-morpholinophenyl)-6-methoxy-7-(3-(2-(2-(2-(2-(2-(2-methacryloxyethoxy)ethoxy)ethoxy)ethoxy)ethoxy)carbonylethyl)carboxymethylenepiperidin-1-yl)-13,13-dimethyl-3H,13H-indeno[2',3':3,4]naphtho[1,2-b]pyran.

Example 9

Step 1

The procedure of Step 4 of Example 4 was followed except that morpholine was used in place of 3-piperidine. After the chromatography, the product was recrystallized from t-butyl methyl ether/hexanes (2/1), yielding off-white crystals.

Step 2

The procedure of Step 3 of Example 7 was followed except that 3-phenyl-3-(4-(2-hydroxyethoxy)phenyl)-6-methoxy-7-morpholino-13,13-dimethyl-3H,13H-indeno[2',3':3,4]naphtho[1,2-b]pyran (from Step 1) was used in place of 3-phenyl-3-(4-methoxyphenyl)-6-methoxy-7-(4-hydroxypiperidin-1-yl)-13,13-dimethyl-3H,13H-indeno[2',3':3,4]naphtho[1,2-b]pyran. The product was obtained as a brown expanded foam.

Step 3

The procedure of Step 4 of Example 7 was followed except that 3-phenyl-3-(4-(2-(2-hydroxycarbonylethyl)carboxy)phenyl)-6-methoxy-7-morpholino-13,13-dimethyl-3H,13H-indeno[2',3':3,4]naphtho[1,2-b]pyran (from Step 2) was used in place of 3-phenyl-3-(4-methoxyphenyl)-6-methoxy-7-(4-(2-hydroxycarbonylethyl)carboxypiperidin-1-yl)-13,13-dimethyl-3H,13H-indeno[2',3':3,4]naphtho[1,2-b]pyran. The product was obtained as an oily mixture. Mass spectrometry indicates the major component is with 5 to 8 ethoxy groups in the ethylene glycol chain including 3-phenyl-3-(4-(2-(2-(2-(2-(2-(2-(2-methacryloxyethoxy)ethoxy)ethoxy)ethoxy)ethoxy)ethoxy)carbonylethyl)carboxyethoxy)phenyl)-6-methoxy-7-morpholino-13,13-dimethyl-3H,13H-indeno[2',3':3,4]naphtho[1,2-b]pyran.

Example 10

Synthesis of Photochromic Polymer Test Square and Photochromic Performance Testing Photochromic Performance Testing The photochromic performance of the photochromic materials of Examples 1-9 was tested as follows.

A quantity of the photochromic material to be tested calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic material was dissolved into the monomer blend by stirring and gentle heating. After a clear solution was obtained, it was poured into a flat sheet mold having the interior dimensions of 2.2 mm×6 inches (15.24 cm)×6 inches (15.24 cm). The mold was sealed and placed in a horizontal airflow, programmable oven programmed to increase the temperature from 40° C. to 95° C. over a 5 hour interval, hold the temperature at 95° C. for 3 hours and then lower it to 60° C. for at least 2 hours. The methacrylate terminated photochromic dyes were copolymerized into the sheet after this period of time. After the mold was opened, the polymer sheet was cut using a diamond blade saw into 2 inch (5.1 cm) test squares.

The photochromic test squares prepared as described above were tested for photochromic response on an optical bench. Prior to testing on the optical bench, the photochromic test squares were exposed to 365 nm ultraviolet light for about 15 minutes to cause the photochromic material to transform from the unactivated (or bleached) state to an activated (or colored) state, and then placed in a 76° C. oven for about 15 minutes to allow the photochromic material to revert back to the bleached state. The test squares were then cooled to room temperature, exposed to fluorescent room lighting for at least 2 hours, and then kept covered (that is, in a dark environment) for at least 2 hours prior to testing on an optical bench maintained at 24° C. The bench was fitted with a 300-watt xenon arc lamp, a remote controlled shutter, a KG-2 filter acting as a heat sink for the arc lamp, and neutral density filter(s). The sample holder in which the square to be tested was situated in a water bath which was kept at 23° C. A collimated beam of light from a tungsten lamp was passed through the square at a small angle (approximately 30°) normal to the square. After passing through the square, the light from the tungsten lamp was directed to a collection sphere, avoiding collecting scattered light and reblend light beam. From the collection sphere the light travels via a fiber optic cable to an Ocean Optics S2000 spectrophotometer where the resulting spectrum was measured at the visible lambda max ("$\lambda_{max-vis}$") of the photochromic material being tested. The $\lambda_{max-vis}$ is the wavelength in the visible spectrum at which the maximum absorption of the activated (colored) form of the photochromic compound in a test square occurs. The $\lambda_{max-vis}$ wavelength was determined by testing the photochromic test squares in a Varian Cary 4000 UV-Visible spectrophotometer. The output signals from the detector were processed by a radiometer.

The saturated optical density ("Sat'd OD") for each test square was determined by opening the shutter from the xenon lamp and measuring the transmittance after exposing the test chip to UV radiation for 30 minutes. The xenon beam is set to 1 W/m² for measurements of this class of dyes, however, in some instances, a power setting of 3 W/m² was used. Irradiance was adjusted by varying the neutral density filter at the light source and by adjusting lamp output. The First Fade Half Life ("$T_{1/2}$") is the time interval in seconds for the absorbance of the activated form of the photochromic material in the test squares to reach one half the Sat'd OD absorbance value at room temperature (24° C.), after removal of the source of activating light. Results for the photochromic materials tested are listed below in Table 1.

TABLE 1

Photochromic Test Data

| Example No. | $\lambda_{max-vis}$ (nm) | Sat'd OD (at $\lambda_{max-vis}$) | $T_{1/2}$ (sec) (at $\lambda_{max-vis}$) |
|---|---|---|---|
| 1 | 502 | 1.09 | 952 |
| 2 | 501 | 1.01 | 836 |
| 3* | 495 | 1.52 | 738 |
| 4 | 475 | 1.37 | 1731 |
| 5 | 612 | 0.94 | 1145 |
| 6* | 587 | 1.21 | 317 |
| 7 | 470 | 1.17 | 1028 |
| 8 | 502 | 1.16 | 780 |
| 9 | 459 | 1.52 | 776 |

*tested under 3 W irradiation

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention, as defined by the appended claims.

We claim:

1. A photochromic material comprising:
   a photochromic naphthopyran; and
   at least one reactive substituent bonded to the photochromic naphthopyran, wherein each reactive substituent is independently represented by one of:

-A-D-E-G-J;

-G-E-G-J;

-D-E-G-J;

-A-D-J;

-D-G-J; and

-D-J;

wherein:
(i) each -A- is independently —C(=O)—, —OC(=O)—, —NHC(=O)—, or —CH$_2$—;
(ii) each -D- is independently:
   (a) a diamine residue or a derivative thereof, said diamine residue being an aliphatic diamine residue, a cyclo aliphatic diamine residue, a diazacycloalkane residue, an azacyclo aliphatic amine residue, a diazacrown ether residue, or an aromatic diamine residue, wherein a first amine nitrogen of said diamine residue forms a bond with -A- or the photochromic naphthopyran, and a second amine nitrogen of said diamine residue forms a bond with -E-, -G-, or -J; or
   (b) an amino alcohol residue or a derivative thereof, said amino alcohol residue being an aliphatic amino alcohol residue, a cyclo aliphatic amino alcohol residue, an azacyclo aliphatic alcohol residue, a diazacyclo aliphatic alcohol residue, or an aromatic amino alcohol residue, wherein an amine nitrogen of said amino alcohol residue forms a bond with -A- or the photochromic naphthopyran, and an alcohol oxygen of said amino alcohol residue forms a bond with -E-, -G-, or -J; or said amine nitrogen of said amino alcohol residue forms a bond with -E-, -G-, or -J, and said alcohol oxygen of said amino alcohol residue forms a bond with -A- or the photochromic naphthopyran;
(iii) each -E- is independently a dicarboxylic acid residue or a derivative thereof, said dicarboxylic acid residue being an aliphatic dicarboxylic acid residue, cycloaliphatic dicarboxylic acid residue, or an aromatic dicarboxylic acid residue, wherein a first carbonyl group of said dicarboxylic acid residue forms a bond with -G- or -D-, and a second carbonyl group of said dicarboxylic acid residue forms a bond with -G-;
(iv) each -G- is independently:
   (a) —[(OC$_2$H$_4$)$_x$(OC$_3$H$_6$)$_y$(OC$_4$H$_8$)$_z$]—O—, wherein x, y, and z, are each independently a number between 0 and 50, and the sum of x, y, and z ranges from 1 to 50; or
   (b) a polyol residue or a derivative thereof, said polyol residue being an aliphatic polyol residue, a cyclo aliphatic polyol residue, and an aromatic polyol residue, wherein a first polyol oxygen of said polyol residue forms a bond with -E-, -D-, or the photochromic naphthopyran, and a second polyol oxygen of said polyol residue forms a bond with -E- or -J; and
(v) each -J is independently a group comprising a reactive moiety or residue thereof; or -J is hydrogen, provided that if -J is hydrogen, -J is bonded to an oxygen of group -D- or -G-, forming a reactive moiety.

2. The photochromic material of claim 1, wherein the photochromic material is purified by recrystallization.

3. The photochromic material of claim 2, wherein r is 1 or 2.

4. The photochromic material of claim 3, wherein the photochromic material comprises two reactive substituents R.

5. The photochromic material of claim 3, wherein R$_3$ comprises a substituent at the 6 and 7 position on structure III or structure IV, said substituent at the 6 and 7 position each being independently: the reactive substituent R; —OR$_{10}$, wherein R$_{10}$ is hydrogen; C$_1$-C$_6$ alkyl; or a nitrogen-containing group, wherein said nitrogen-containing group is:
   (i) —N(R$_{11}$)R$_{12}$ wherein R$_{11}$ and R$_{12}$ are each independently hydrogen, C$_1$-C$_8$ alkyl, phenyl, or C$_1$-C$_{20}$ alkoxyalkyl, or
   (ii) a nitrogen containing ring represented by the following graphic formula VA:

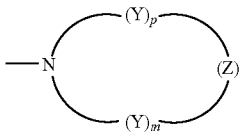

wherein each —Y— is independently chosen for each occurrence from —$CH_2$—, —$CH(R_{13})$—, —$C(R_{13})_2$—, —CH(aryl)-, —$C(aryl)_2$-, and —$C(R_{13})$(aryl)-, and Z is —Y—, —O—, —S—, —S(O)—, —$SO_2$—, —NH—, —$N(R_{13})$—, or —N(aryl)-, wherein each $R_{13}$ is independently $C_1$-$C_6$ alkyl, each aryl is independently phenyl or naphthyl, m is the integer 1, 2 or 3, and p is the integer 0, 1, 2, or 3 and when p is 0, Z is —Y—.

6. The photochromic material of claim 3, wherein $R_5$ and $R_6$ are each independently the reactive substituent R; $C_1$-$C_6$ alkyl; hydroxy; or —$OR_{18}$, wherein $R_{18}$ is $C_1$-$C_6$ alkyl.

7. A photochromic article comprising;
a substrate; and
the photochromic material according to claim 1 connected to at least a portion of the substrate.

8. The photochromic article of claim 7, wherein the photochromic article is an ophthalmic element, said ophthalmic element being at least one of a corrective lens, a non-corrective lens, a magnifying lens, a protective lens, a visor, goggles, or a lens for an optical instrument.

9. The photochromic article of claim 8 wherein an at least partial coating of a polymeric material is connected to at least a portion of a surface of the substrate and the polymeric material comprises the photochromic material.

10. The photochromic article of claim 7, wherein the substrate comprises a polymeric material and the photochromic material is at least one of blended with at least a portion of the polymeric material of the substrate and bonded to at least a portion of the polymeric material of the substrate.

11. The photochromic article of claim 10, wherein the photochromic material is bonded by co-polymerization with at least a portion of the polymeric material of the substrate.

12. The photochromic article of claim 7, wherein the photochromic article is an optical element, said optical element being at least one of an ophthalmic element, a display element, a window, a mirror, an active liquid crystal cell element, or a passive liquid crystal cell element.

13. The photochromic article of claim 7, wherein the photochromic article comprises at least one of a complementary photochromic material, a photoinitiator, a thermal initiator, a polymerization inhibitor, a solvent, a light stabilizer, a heat stabilizer, a mold release agent, a rheology control agent, a leveling agent a free radical scavenger, and an adhesion promoter.

14. The photochromic article of claim 7, wherein an at least partial coating or film is connected to at least a portion of the substrate, the at least partial coating or film being at least one of a primer coating or film, a protective coating or film, an anti-reflective coating or film, a conventional photochromic coating or film, and a polarizing coating or film.

15. A method of making a photochromic article comprising connecting a photochromic material according to claim 1 to at least a portion of a substrate.

16. The method according to claim 15, wherein the substrate comprises a polymeric material, and connecting comprises incorporating the photochromic material into at least a portion of the substrate by at least one of blending the photochromic material with at least a portion of the polymeric material of the substrate and bonding the photochromic material to at least a portion of the polymeric material of the substrate.

17. The method according to claim 16, wherein the photochromic material is bonded by co-polymerizing the photochromic material with at least a portion of the polymeric material of the substrate.

18. The method according to claim 16, wherein the substrate comprises a polymeric material and connecting the photochromic material into at least a portion of a substrate comprises casting-in-place the photochromic material and the polymeric material.

19. The method according to claim 15, wherein the substrate comprises a polymeric material or a glass and connecting a photochromic material to at least a portion of a substrate, comprises applying an at least partial coating comprising the photochromic material to at least a portion of the substrate.

20. The method according to claim 19, wherein applying the at least partial coating comprising the photochromic material to at least a portion of the substrate comprises one of spin coating, roll coating, spray coating, curtain coating, and in-mold casting.

21. A photochromic composition comprising
a polymeric material; and
a photochromic material according to claim 1 incorporated into at least a portion of said
polymeric material.

22. The photochromic composition of claim 21, wherein the polymeric material is polyacrylates, polymethacrylates, poly($C_1$-$C_{12}$)alkylated methacrylates, polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral, or polymers of members of polyol(allyl carbonate)monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers, diallyidene pentaerythritol monomers, and combinations thereof.

23. The photochromic composition of claim 21, wherein the polymeric material is an acrylate, a methacrylate, methyl methacrylate, ethylene glycol his methacrylate, thoxylated bisphenol A dimethacrylate, vinyl acetate, vinylbutyral, urethane, thiourethane, diethylene glycol, bis(allyl carbonate), diethylene glycol dimethacrylate, diisopropenyl benzene, ethoxylated trimethylol propane triacrylate, and combinations thereof.

24. The photochromic composition of claim 21, wherein the photochromic composition comprises at least one of a complementary photochromic material, a photoinitiator, a thermal initiator, a polymerization inhibitor, a solvent, a light stabilizer, a heat stabilizer, a mold release agent, a rheology control agent, a leveling agent a free radical scavenger, and an adhesion promoter.

25. The photochromic composition of claim 21, wherein the photochromic composition is a coating composition.

26. The photochromic material of claim 1, wherein the photochromic naphthopyran is a 2H-naphtho[1,2-b]pyran, a 3H-naphtho[2,1-b]pyran, an indeno[2',3':3,4]naphtho[1,2-b]pyran, an indeno[1',2':4,3]naphtho[1,2-b]pyran, or a mixture thereof.

27. The photochromic material of claim 1, wherein each -J is independently acryl, crotyl, methacryl, 2-(methacryloxy) ethylcarbamyl, 2-(methacryloxy)ethoxycarbonyl, 4-vinylphenyl, vinyl, 1-chlorovinyl, or epoxy.

28. A photochromic material represented by:

PC—[R]$_r$ wherein (a) PC comprises a photochromic naphthopyran wherein said photochromic naphthopyran is a 2H-naphtho[1,2-b]pyran, a 3H-naphtho[2,1-b]pyran, an indeno[2',3':3,4]naphtho[1,2-b]pyran, an indeno[1',2':4,3]naphtho[2,1-b]pyran, or a mixture thereof;

(b) r is an integer ranging from 1 to 4; and (c) each R group is a reactive substituent independently represented by one of:

-A-D-E-G-J;

-G-E-G-J;

-D-E-G-J;

-A-D-J;

-D-G-J; and wherein:

(i) each -A- is independently —C(=O)—, —OC(=O)—, —NHC(=O)—, or —CH$_2$—;

(ii) each -D- is independently:
  (a) a diamine residue or a derivative thereof, said diamine residue being an aliphatic diamine residue, a cyclo aliphatic diamine residue, a diazacycloalkane residue, an azacyclo aliphatic amine residue, a diazacrown ether residue, or an aromatic diamine residue, wherein a first amine nitrogen of said diamine residue forms a bond with -A- or PC, and a second amine nitrogen of said diamine residue forms a bond with -E-, -G-, or -J; or
  (b) an amino alcohol residue or a derivative thereof, said amino alcohol residue being an aliphatic amino alcohol residue, a cyclo aliphatic amino alcohol residue, an azacyclo aliphatic alcohol residue, a diazacyclo aliphatic alcohol residue, or an aromatic amino alcohol residue, wherein an amine nitrogen of said amino alcohol residue forms a bond with -A- or PC, and an alcohol oxygen of said amino alcohol residue forms a bond with -E-, -G-, or -J; or said amine nitrogen of said amino alcohol residue forms a bond with -E-, -G-, or -J, and said alcohol oxygen of said amino alcohol residue forms a bond with -A- or PC;

(iii) each -E- is independently a dicarboxylic acid residue or a derivative thereof, said dicarboxylic acid residue being an aliphatic dicarboxylic acid residue, a cycloaliphatic dicarboxylic acid residue, or an aromatic dicarboxylic acid residue, wherein a first carbonyl group of said dicarboxylic acid residue forms a bond with -G- or -D-, and a second carbonyl group of said dicarboxylic acid residue forms a bond with -G-;

(iv) each -G- is independently:
  (a) —[(OC$_2$H$_4$)$_x$(OC$_3$H$_6$)$_y$(OC$_4$H$_8$)$_z$]—O—, wherein x, y, and z, are each independently a number between 0 and 50, and the sum of x, y, and z ranges from 1 to 50; or (b) a polyol residue or a derivative thereof, said polyol residue being an aliphatic polyol residue, a cyclo aliphatic polyol residue, or an aromatic polyol residue, wherein a first polyol oxygen of said polyol residue forms a bond with -E-, -D-, or PC, and a second polyol oxygen of said polyol residue forms a bond with -E- or -J; and (v) each -J is independently a group comprising acryl, crotyl, methacryl, 2-(methacryloxy)ethylcarbamyl, 2-(methacryloxy)ethoxycarbonyl, 4-vinylphenyl, vinyl, 1-chlorovinyl, or epoxy; or -J is hydrogen, provided that if -J is hydrogen, -J is bonded to an oxygen of group -D- or -G-.

29. A photochromic material represented by:

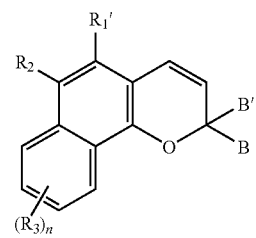

I

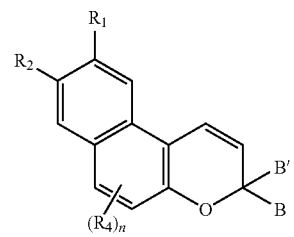

II

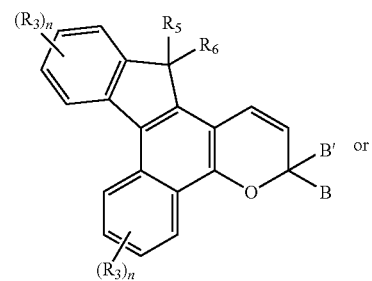

III

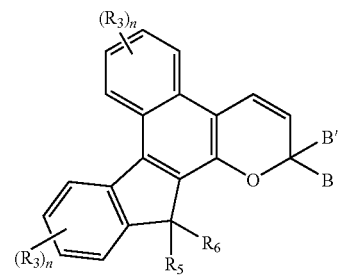

IV or a mixture thereof, wherein, (a) R$_1$ is:

a reactive substituent R, wherein said reactive substituent R is represented by one of:

-A-D-E-G-J;

-G-E-G-J;

-D-E-G--J;

-A-D-J;

-D-G-J; and

-D-J;

wherein

-A- is —C(=O)—, —OC(=O)—, —NHC(=O)—, or —CH$_2$—;

-D- is: a diamine residue or a derivative thereof, said diamine residue being an aliphatic diamine residue, a cyclo aliphatic diamine residue, a diazacycloalkane residue, an azacyclo aliphatic amine residue, a diazacrown ether residue, or an aromatic diamine residue, wherein a first amine nitrogen of said diamine residue forms a bond with -A-, structure I, structure II, structure III, or structure IV, and a second amine nitrogen of said diamine residue forms a bond with -E-, -G-, or -J; or an amino alcohol residue or a derivative thereof, said amino alcohol residue being an aliphatic amino alcohol residue, a cyclo aliphatic amino alcohol residue, an azacyclo aliphatic alcohol residue, a diazacyclo aliphatic alcohol residue, or an aromatic amino alcohol residue, wherein an amine nitrogen of said amino alcohol residue forms a bond with -A-, structure I, structure II, structure III, or structure IV, and an alcohol oxygen of said amino alcohol residue forms a bond with -E-, -G-, or -J; or said amine nitrogen of said amino alcohol residue forms a bond with -E-, -G-, or -J, and said alcohol oxygen of said amino alcohol residue forms a bond with -A-, structure I, structure II, structure III, or structure IV;

-E- is a dicarboxylic acid residue or a derivative thereof, said dicarboxylic acid residue being an aliphatic dicarboxylic acid residue, a cycloaliphatic dicarboxylic acid residue, or an aromatic dicarboxylic acid residue, wherein a first carbonyl group of said dicarboxylic acid residue forms a bond with -G- or -D-, and a second carbonyl group of said dicarboxylic acid residue forms a bond with -G-;

each -G- is independently: -[(OC$_2$H$_4$)$_x$(OC$_3$H$_6$)$_y$(OC$_4$H$_8$)$_z$]—O—, wherein x, y, and z, are each independently a number between 0 and 50, and the sum of x, y, and z ranges from 1 to 50; or a polyol residue or a derivative thereof, said polyol residue being an aliphatic polyol residue, a cyclo aliphatic polyol residue, or an aromatic polyol residue, wherein a first polyol oxygen of said polyol residue forms a bond with -E-, -D-, structure I, structure II, structure III, or structure IV, and a second polyol oxygen of said polyol residue forms a bond with -E- or -J; and -J is a group comprising acryl, methacryl, crotyl, 2-(methacryloxy)ethylcarbamyl, 2-(methacryloxy)ethoxycarbonyl, 4-vinylphenyl, vinyl, 1-chlorovinyl, or epoxy, or -J is hydrogen, provided that if -J is hydrogen, -J is bonded to an oxygen of group -D- or -G-;

or R$_1$ is hydrogen; hydroxy; C$_1$-C$_3$ alkyl; or the group —C(=O)W, wherein W is —OR$_7$, —N(R$_8$)R$_9$, piperidino or morpholino, wherein R$_7$ is allyl, C$_1$-C$_6$ alkyl, phenyl, mono(C$_1$-C$_6$)alkyl substituted phenyl, mono (C$_1$-C$_6$)alkoxy substituted phenyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl, C$_1$-C$_6$ alkoxy(C$_2$-C$_4$)alkyl or C$_1$-C$_6$ haloalkyl, R$_8$ and R$_9$ are each independently C$_1$-C$_6$ alkyl, alkyl, C$_5$-C$_7$ cycloalkyl, phenyl, mono-substituted phenyl, or di-substituted phenyl, wherein said phenyl substituents are C$_1$-C$_6$ alkyl or C$_1$-C$_6$ alkoxy, and said halo substituent is chloro or fluoro;

(b) R$_1$' is: the reactive substituent R; hydrogen; hydroxy; C$_1$-C$_3$ alkyl; or the group —C(=O)W, wherein W is —OR$_7$, —N(R$_8$)R$_9$, piperidino or morpholino, wherein R$_7$ is allyl, C$_1$-C$_6$ alkyl, phenyl, mono(C$_1$-C$_6$)alkyl substituted phenyl, mono(C$_1$-C$_6$)alkoxy substituted phenyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl, C$_1$-C$_6$ alkoxy(C$_2$-C$_4$)alkyl or C$_1$-C$_6$ haloalkyl, and R$_8$ and R$_9$ are each independently C$_1$-C$_6$ alkyl, C$_5$-C$_7$ cycloalkyl, phenyl, mono-substituted phenyl, or di-substituted phenyl, wherein said phenyl substituents are C$_1$-C$_6$ alkyl or C$_1$-C$_6$ alkoxy, and said halo substituent is chloro or fluoro;

(c) R$_2$ is: the reactive substituent R; hydrogen; C$_1$C$_6$ alkyl; C$_3$-C$_7$ cycloalkyl; substituted or unsubstituted phenyl; or —OR$_{10}$ or —OC(=O)R$_{10}$, wherein R$_{10}$ is hydrogen, C$_1$-C$_6$ alkyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl, (C$_1$-C$_6$)alkoxy(C$_2$-$_4$) alkyl, C$_3$-C$_7$ cycloalkyl, or mono(C$_1$-C$_4$)alkyl substituted C$_3$-C$_7$ cycloalkyl, and said phenyl substituents are C$_1$-C$_6$ alkyl or C$_1$-C$_6$ alkoxy;

(d) n is an integer ranging from 0 to 4, where R$_3$ and R$_4$ are independently for each occurrence: the reactive substituent R; hydrogen; fluoro; chloro; C$_1$-C$_6$ alkyl; C$_3$-C$_7$ cycloalkyl; substituted or unsubstituted phenyl; —OR$_{10}$ or —OC(=O)R$_{10}$, wherein R$_{10}$ is hydrogen, C$_1$-C$_6$ alkyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl, (C$_1$-C$_6$)alkoxy(C$_2$-C$_4$) alkyl, C$_3$-C$_7$ cycloalkyl, or mono(C$_1$-C$_4$)alkyl substituted C$_3$-C$_7$ cycloalkyl, and said phenyl substituents are C$_1$C$_6$ alkyl or C$_1$-C$_6$ alkoxy; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or a derivative thereof, —CH$_2$—, —(CH$_2$)$_t$—, or —[O—(CH$_2$)$_t$]$_k$—, wherein t is the integer 2, 3, 4, 5 or 6 and k is an integer from 1 to 50, the substituent being connected to an aryl group on another photochromic material; —N(R$_{11}$)R$_{12}$, wherein R$_{11}$ and R$_{12}$ are each independently hydrogen, C$_1$-C$_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, C$_1$-C$_8$ alkylaryl, C$_3$-C$_{20}$ cycloalkyl, C$_4$-C$_{20}$ bicycloalkyl, C$_5$-C$_{20}$ tricycloalkyl or C$_1$-C$_{20}$ alkoxyalkyl, wherein said aryl group is phenyl or naphthyl, or R$_{11}$ and R$_{12}$ come together with the nitrogen atom to form a C$_3$-C$_{20}$ heterobicycloalkyl ring or a C$_4$-C$_{20}$ hetero-tricycloalkyl ring; a nitrogen containing ring represented by the following graphic formula VA:

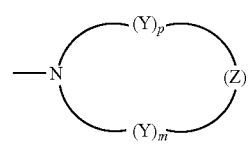

VA wherein each —Y— is independently chosen for each occurrence from —CH$_2$—, —CH(R$_{13}$)—, —C(R$_{13}$)$_2$—, —CH(aryl)-, —C(aryl)$_2$-, and —C(R$_{13}$)(aryl)-, and Z is —Y—, —O—, —S—, —SO$_2$—, —NH—, —N(R$_{13}$)—, or —N(aryl)-, wherein each $R_{13}$ is independently $C_1$-$C_6$ alkyl, each aryl is independently phenyl or naphthyl, m is an integer 1, 2 or 3, and p is an integer 0, 1, 2, or 3 and when p is 0, Z is —Y—; a group represented by one of the following graphic formulae VB or VC:

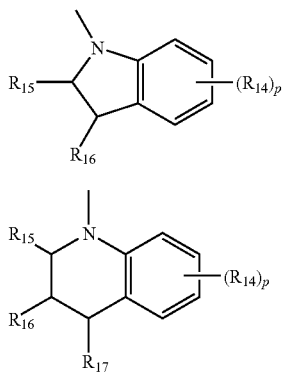

(VB)

(VC)

wherein $R_{15}$, $R_{16}$, and $R_{17}$ are each independently hydrogen, $C_1$-$C_6$ alkyl, phenyl, or naphthyl, or the groups $R_{15}$ and $R_{16}$ together form a ring of 5 to 8 carbon atoms and each $R_{14}$ is independently for each occurrence from $C_1$-$C_6$ alkyl, $C_1$-$C_6$ alkoxy, fluoro or chloro and p is an integer 0, 1, 2, or 3; and unsubstituted, mono-, or di-substituted $C_4$-$C_{18}$ spirobicyclic amine, or unsubstituted, mono, and di-substituted $C_4$-$C_{18}$ spirotricyclic amine, wherein said substituents are independently aryl, $C_1$-$C_6$ alkyl, $C_1$-$C_6$ alkoxy, or phenyl($C_1$-$C_6$) alkyl; or an $R_3$ group in the 6-position and an $R_3$ group in the 7-position together form a group represented by one of VD and VE:

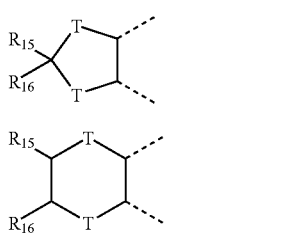

(VD)

(VE)

wherein T and T' are each independently oxygen or the group —$NR_{11}$—, where $R_{11}$, $R_{15}$, and $R_{16}$ are as set forth above;

(e) $R_5$ and $R_6$ are each independently: the reactive substituent R; hydrogen; hydroxy; $C_1$-$C_6$ alkyl; $C_3$-$C_7$ cycloalkyl; allyl; substituted or unsubstituted phenyl; substituted or unsubstituted benzyl; chloro; fluoro; the group —C(=O)W', wherein W' is hydrogen, hydroxy, $C_1$-$C_6$ alkyl, $C_1$-$C_6$ alkoxy, the unsubstituted, mono-or di-substituted aryl groups phenyl or naphthyl, phenoxy, mono- or di-($C_1$-$C_6$)alkoxy substituted phenoxy, mono- or di-($C_1$-$C_6$)alkoxy substituted phenoxy, amino, mono ($C_1$-$C_6$)alkylamino, di($C_1$-$C_6$)alkylamino, phenylamino, mono- or di-($C_1$-$C_6$)alkyl substituted phenylamino, or mono- or di-( $C_1$-$C_6$)alkoxy substituted phenylamino; —$OR_{18}$, wherein $R_{18}$ is $C_1$-$C_6$ alkyl, phenyl($C_1$-$C_3$)alkyl, mono($C_1$-$C_6$)alkyl substituted phenyl ($C_1$-$C_3$)alkyl, mono($C_1$-$C_6$)alkoxy substituted phenyl ($C_1$-$C_3$)alkyl, $C_1$-$C_6$ alkoxy($C_2$-$C_4$alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, or the group —CH($R_{19}$)Y', wherein $R_{19}$ is hydrogen or $C_1$-$C_3$ alkyl and Y' is CN, $CF_3$, or $COOR_{20}$, wherein $R_{20}$ is hydrogen or $C_1$-$C_3$ alkyl, or $R_{18}$ is the group, —C(=O)W", wherein W" is hydrogen, $C_1$-$C_6$ alkyl, $C_1$-$C_6$ alkoxy, the unsubstituted, mono- or di-substituted aryl groups phenyl or naphthyl, phenoxy, mono-, or di-($C_1$-$C_6$)alkyl substituted phenoxy, mono- or di-($C_1$-$C_6$)alkoxy substituted phenoxy, amino, mono($C_1$-$C_6$) alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, wherein each of said phenyl, benzyl, or aryl group substituents are independently $C_1$-$C_6$ alkyl or $C_1$-$C_6$ alkoxy; or a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —$CH_2$—, —$(CH_2)_t$—, or —[O—$(CH_2)_t]_k$—, wherein t is from an integer 2, 3, 4, 5 or 6 and k is an integer from 1 to 50, the substituent being connected to an aryl group on another photochromic material; or $R_5$ and $R_6$ together form an oxo group, a spirocarbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 beuzene rings; and (f) B and B' are each independently: a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is the reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently: hydroxyl, a group —C(=O)$R_{21}$, wherein $R_{21}$ is —$OR_{22}$, —N($R_{23}$)$R_{24}$, piperidino, or morpholino, wherein $R_{22}$ is allyl, $C_1$-$C_6$ alkyl, phenyl, mono($C_1$-$C_6$) alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$) alkyl or $C_1$-$C_6$ haloalkyl, $R_{23}$ and $R_{24}$ are each independently $C_1$-$C_6$ alkyl, $C_5$-$C_7$ cycloalkyl, phenyl or substituted phenyl, the phenyl substituents being $C_1$-$C_6$ alkyl or $C_1$-$C_6$ alkoxy, and said halo substituent is chloro or fluoro, aryl, mono($C_1$-$C_{12}$)alkoxyaryl, di($C_1$-$C_{12}$) alkoxyaryl, mono($C_1$-$C_{12}$)alkylaryl, di($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$) alkyl, $C_3$-$C_7$ cycloalkyloxy($C_1$-$C_{12}$)alkoxy, aryl($C_1$-$C_{12}$)alkyl, aryl($C_1$-$C_{12}$)alkoxy, aryloxy, aryloxy($C_1$-$C_{12}$)alkyl, aryloxy($C_1$-$C_{12}$)alkoxy, mono- or di($C_1$-$C_{12}$) alkylaryl($C_1$-$C_{12}$)alkyl, mono- or di-($C_1$-$C_{12}$) alkoxyaryl($C_1$-$C_{12}$)alkyl, mono- or di-($C_1$-$C_{12}$) alkylaryl($C_1$-$C_{12}$)alkoxy, mono- or di-($C_1$-$C_{12}$)

alkoxyaryl($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, or halogen; an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{12}$ alkyl, $C_1$-$C_{12}$ alkoxy, phenyl, or halogen; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —$CH_2$—, —$(CH_2)_t$—, or —$[O—(CH_2)_t]_k$—, wherein t is an integer 2, 3, 4, 5 or 6 and k is an integer from 1 to 50, the substituent being connected to an aryl group on another photochromic material; a group represented by one of:

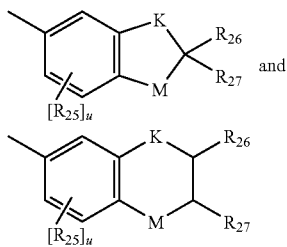

wherein K is —$CH_2$— or —O—, and M is —O— or substituted nitrogen, provided that when M is substituted nitrogen, K is —$CH_2$—, the substituted nitrogen substituents being hydrogen, $C_1$-$C_{12}$ alkyl, or $C_1$-$C_{12}$ acyl, each $R_{25}$ being independently chosen for each occurrence from $C_1$-$C_{12}$ alkyl, $C_1$-$C_{12}$ alkoxy, hydroxy, and halogen, $R_{26}$ and $R_{27}$ each being independently hydrogen or $C_1$-$C_{12}$ alkyl, and u is an integer ranging from 0 to 2; or a group represented by;

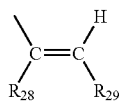

wherein $R_{28}$ is hydrogen or $C_1$-$C_{12}$ alkyl, and $R_{29}$ is an unsubstituted, mono-, or di-substituted group chosen from naphthyl, phenyl, furanyl, and thienyl, wherein the substituents are $C_1$-$C_{12}$ alkyl, $C_1$-$C_{12}$ alkoxy, or halogen; or B and B' taken together form one of a fluoren-9-ylidene, mono-, or di-substituted fluoren-9-ylidene, each of said fluoren-9-ylidene substituents being independently chosen from $C_1$-$C_{12}$ alkyl, $C_1$-$C_{12}$ alkoxy, and halogen;

provided that the photochromic material comprises at least one reactive substituent R.

30. A photochromic material chosen from:
(i) 3,3-di(4-methoxyphenyl)-6-methoxy-7-(3-(2-methacryloxyethyl)carbamyloxymethylenepiperidin-1-yl)-13,13-dimethyl-3H, 13H-indeno[2',3':3,4]naphtho[1,2-b]pyran;

(ii) 3-phenyl-3-(4-morpholinophenyl)-6-methoxy-7-(3-(2-methacryloxyethyl)carbamyloxymethylenepiperidin-1-yl)-13,13-dimethyl-3H, 13H-indeno [2',3':3,4]naphtho[1,2-b]pyran;

(iii) 3-phenyl-3-(4-(4-phenylpiperazino)phenyl)-6-methoxy-7-(4-(2-methacryloxyethyl)carbamyloxypiperidin-1-yl)-13,13-dimethyl-3H, 13H-indeno[2',3':3,4]naphtho[1,2-b]pyran;

(iv) 3-(4-fluorophenyl)-3-(4-methoxyphenyl)-6-methoxy-7-(4-(2-methacryloxyethyl)carbamyloxypiperidin-1-yl)-13,13-dimethyl-3H, 13-H-indeno[2',3':3,4]naphtho[1,2-b]pyran;

(v) 3-(4-fluorophenyl)-3-(4-morpholinophenyl)-6-methoxy-7-(4-(2-methacryloxyethyl)carbamyloxypiperidin-1-yl)-13,13-dimethyl-3H, 13H-indeno[2',3':3,4]naphtho[1,2-b]pyran;

(vi) 3-phenyl-3-(4-morpholinophenyl)-6-methoxy-7-(4-(2-methacryloxyethyl)carbamyloxypiperidin-1-yl)-13,13-dimethyl-3H, 13H-indeno[2',3':3,4]naphtho [1,2-b]pyran;

(vii) 3-phenyl-3-(4-morpholinophenyl)-6-methoxy-7-(4-(2-methacryloxyethyl)carbamylpiperazin-1-yl)-13,13-dimethyl-3H, 13H-indeno[2',3':3,4]naphtho [1,2-b]pyran;

(ix) 3-phenyl-3-(4-methoxyphenyl)-6-methoxy-7-(4-(2-methacryloxyethyl)carbamylpiperazin-1-yl)-13,13-dimethyl-3H, 13H-indeno[2',3':3,4]naphtho[1,2-b]pyran;

(xi) 3-phenyl-3-(4-(4-(2-methacryloxyethyl)carbamylpiperazin-1yl)phenyl)-6,11-dimethoxy-13,13-dimethyl-3H, 13H-indeno[2',3':3,4]naphtho[1,2-b]pyran;

(xiii) 3-phenyl-3-(4-morpholinophenyl)-6-methoxy-7-(3-(2-(2-(2-(2-(2-(2-methacryloxyethoxy)ethoxy)ethoxy)ethoxy)ethoxy)carbonylethyl)carboxymethylenepiperidin-1-yl)-13,13-dimethyl-3H, 13H-indeno[2',3':3,4]naphtho[1,2-b]pyran;

(xiv) 3-phenyl-3-(4-methoxyphenyl)-6-methoxy-7-(2-(2-(2-(2-(2-(2-methacryloxyethoxy)ethoxy)ethoxy)ethoxy)ethoxy)carbonylethyl)carboxymethylenepiperidin-1-yl)-13,13-dimethyl-3H, 13H-indeno[2',3':3,4]naphtho[1,2-b]pyran;

(xv) 3-phenyl-3-(4-morpholinophenyl)-6-methoxy-7-(4-(2-(2-(2-(2-(2-(2-methacryloxyethoxy)ethoxy)ethoxy)ethoxy)ethoxy)carbonylethyl)carboxypiperidin-1-yl)-13,13-dimethyl-3H-13H-indeno[2',3':3,4]naphtho[1,2-b]pyran;

(xvi) 3-phenyl-3-(4-methoxyphenyl)-6-methoxy-7-(4-(2-(2-(2-(2-(2-(2-methacryloxyethoxy)ethoxy)ethoxy)ethoxy)ethoxy)carbonylethyl)carboxypiperidin-1-yl)-13,13-dimethyl-3H-13H-indeno[2',3':3,4]naphtho[1,2-b]pyran;

(xvii) 3-phenyl-3-(4-(2-(2-(2-(2-(2-(2-(2-(2-methacryloxyethoxy)ethoxy)ethoxy)ethoxy)ethoxy)ethoxy)carbonylethyl)carboxyethoxy)phenyl)-6-methoxy-7-morpholino-13,13-dimethyl-3H, 13H-indeno[2',3':3,4]naphtho[1,2-b]pyran;

(xviii) 3-phenyl-3-(4-(4-(2-(2-methacryloxyethyl)carbamyloxyethyl)piperazin-1-yl)phenyl)-13,13-dimethyl-3H, 13H-indeno[2',3':3,4]naphtho[1,2-b]pyran;

and combinations thereof.

* * * * *